(12) United States Patent
Koyama et al.

(10) Patent No.: US 6,284,801 B1
(45) Date of Patent: *Sep. 4, 2001

(54) ANTIRHEUMATIC AGENTS

(75) Inventors: Nobuto Koyama; Hua-Kang Wu; Takanari Tominaga; Eiji Nishiyama; Michio Hagiya; Tatsuji Enoki; Hiromu Ohnogi; Ikunoshin Kato, all of Otsu (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/380,239

(22) PCT Filed: Mar. 10, 1998

(86) PCT No.: PCT/JP98/01149

§ 371 Date: Aug. 27, 1999

§ 102(e) Date: Aug. 27, 1999

(87) PCT Pub. No.: WO98/43623

PCT Pub. Date: Oct. 8, 1999

(30) Foreign Application Priority Data

| Apr. 1, 1997 | (JP) | ................................................. | 9-096399 |
| Jun. 6, 1997 | (JP) | ................................................. | 9-163473 |
| Aug. 25, 1997 | (JP) | ................................................. | 9-241680 |
| Oct. 1, 1997 | (JP) | ................................................. | 9-283204 |
| Dec. 12, 1997 | (JP) | ................................................. | 9-362273 |

(51) Int. Cl.⁷ ................................................. A61K 31/12
(52) U.S. Cl. ........................ 514/690; 426/531; 426/590; 426/625; 426/653
(58) Field of Search ........................ 514/690; 426/590, 426/531, 625, 653

(56) References Cited

U.S. PATENT DOCUMENTS

| 5,149,711 | 9/1992 | Hazato et al. | ........................ | 514/548 |
| 6,087,401 | 7/2000 | Koyama et al. | ........................ | 514/690 |

FOREIGN PATENT DOCUMENTS

| 0 974 347 | 1/2000 | (EP) . |
| 0 978 277 | 2/2000 | (EP) . |
| 0 978 278 | 2/2000 | (EP) . |
| 1 008 345 | 6/2000 | (EP) . |
| WO98/13328 | 2/1998 | (JP) . |

OTHER PUBLICATIONS

Ahmad et al, "On the formation of reductic acid from pentoses or hexuronic acids", Carbohydrate Research (1993), 247, pp. 217–222, Apr. 1993.*

Cocu et al, "Research on the series of cyclitols XLIV. Synthesis of cyclose derivatives of cyclopentane", Helvita Chimica Acta (1972), 55(8), pp. 2838–2844, Dec. 1972.*

Wilson et al., Ann. N.Y. Acad. Sci., vol. 804, pp. 276–283 (abstract). (1997),

Translation of Japanese Patent Publication (Kokai) No. Sho–50–70597 (1995).

European Search Report (2000).

* cited by examiner

*Primary Examiner*—Frederick Krass
(74) *Attorney, Agent, or Firm*—Kennedy, Covington, Lobdell & Hickman, LLP

(57) ABSTRACT

An antirheumatic agent which is characterized in containing at least one compound selected from a group consisting of 4,5-dihydroxy-2-cyclopenten-1-one represented by the following formula [I] and an optically active substance and a salt thereof as an effective component.

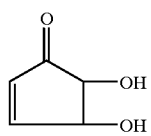

[I]

4 Claims, 14 Drawing Sheets

ANTIRHEUMATIC AGENTS

This appln. is a 371 of PCT/JP98,01149 filed Mar. 18, 1998.

TECHNICAL FIELD OF THE INVENTION

The present invention relates to pharmaceuticals, foods and beverages useful for therapy and prevention of inflammatory diseases such as chronic articular rheumatism.

PRIOR ART

Inflammation is believed to be a result where living body defensively acts against the invasion from outside and produces intrinsic active substance to adapt the state of the body thereto. There are many cases, however, that the reaction induced thereby is harmful and induces a diseased state. In addition, inflammation in autoimmune diseases is resulted from the fact that immunocytes regard themselves as foreign matters and act in an interceptive manner even to normal cells.

It has been reported that, in helper T (Th) cells, there are Th1 cells which produce interleukin-2 and interferon γ (IFN-γ) which are cytokines promoting the activation of cellular immunity such as macrophage (Mø) and also Th2 cells which produce interleukin-4, interleukin-5 and interleukin-10 activating the humoral immunity participated in antibody production.

It has been also shown that Th1 cells and Th2 cells are controlled each other by cytokines produced by each of them. Thus, IFN-γ produced by Th1 cells controls the activation of Th2 cells and induces the activation of Th1 cells. On the other hand, interleukin-10 produced by Th2 cells controls the activation of Th1 cells and interleukin-4 induces the activation of Th2 cells.

Autoimmune diseases are roughly classified into organ-specific and systemic ones. It is believed that, in systemic autoimmune disease and allergic disease, the symptom is caused by Th2-dominant immune response while, in organ-specific autoimmune disease and inflammatory disease, the symptom is caused by Th1-dominant immune response.

Chronic articular rheumatism which is one of autoimmune diseases is believed to be inflammation specific in articular site and is suggested probably to be an organ-specific disease or, in other words, Th1-mediated autoimmune. Actually, in inflammation sites of patients suffering from rheumatism, invasion of Mø and neutrophils which are believed to be induced and activated by cytokines derived from Th1 and significant increase in tumor necrosis factor-α produced by Mø are noted. In other organ-specific autoimmune diseases and inflammatory diseases, the same histologic patterns are observed as well and it is believed that inflammation is exacerbated by those inflammatory cells and inflammatory cytokines which are induced by Th1.

From those facts, it is believed that, in the therapy of inflammatory diseases and organ-specific autoimmune diseases such as chronic articular rheumatism, suppression of tumor necrosis factor produced from Mø and induction of interleukin-10 which is a Th1-inhibiting cytokine are important [Igaku no Ayumi, published by Ishiyaku Shuppan KK, volume 182, pages 523–528 and 661–665 (1997)].

As a drug therapy for chronic articular rheumatism, an internal therapy by steroids, non-steroidal anti-inflammatory agents and remission-inducing agents such as gold and D-penicillamine have been conducted.

PROBLEMS TO BE SOLVED BY THE INVENTION

An object of the present invention is to develop a compound which is useful for the therapy of inflammatory diseases such as chronic articular rheumatism and to offer pharmaceuticals, foods and beverages containing said compound.

MEANS TO SOLVE THE PROBLEM

In order to achieve the above-mentioned object, the present inventors have conducted an intensive investigation and found that 4,5-dihydroxy-2-cyclopenten-1-one which is represented by the formula [I] (hereinafter, just referred to as "the cyclopentenone") is useful for therapy or prevention of inflammatory diseases such as chronic articular rheumatism and immune diseases whereupon the present invention has been accomplished.

Outline of the present invention is that the first feature of the present invention relates to an antirheumatic agent which is characterized in containing at least one compound selected from a group consisting of 4,5-dihydroxy-2-cyclopenten-1-one represented by the following formula [I] and an optically active substance and a salt thereof as an effective component.

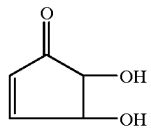

[I]

The second feature of the present invention relates to food or beverage for the improvement or prevention of chronic articular rheumatism which is characterized in containing at least one compound selected from a group consisting of 4,5-dihydroxy-2-cyclopenten-1-one represented by the formula [I] and an optically active substance and a salt thereof as an effective component.

EMBODIMENTS OF THE INVENTION

Figure 1:
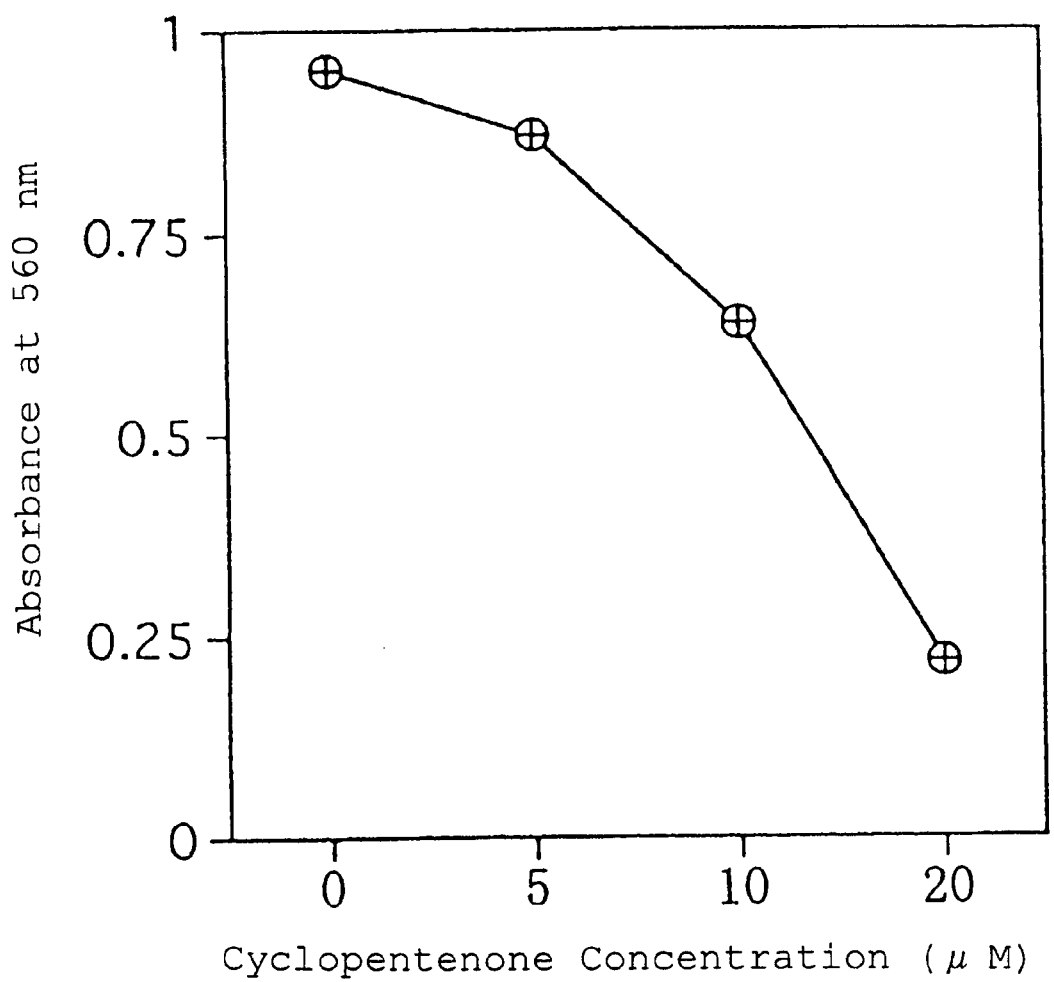
FIG. 1 shows an influence of cyclopentenone on the growth of Jurkat cells.

The present invention will now be specifically illustrated as hereinafter.

The cyclopentenone represented by the formula [I] used in the present invention covers both isomers where the configurations of hydroxyl groups at 4- and 5-positions are cis and trans. In the present invention, any of cis-cyclopentenone, trans-cyclopentenone and a mixture of cis- and trans-cyclopentenone may be used. It is also possible to use optically active substances thereof.

cis-Cyclopentenone may be prepared by a chemical synthesis [Helvetica Chimica Acta, volume 55, pages 2838–2844 (1972)]. trans-Cyclopentenone may be prepared either by a chemical synthesis [Carbohydrate Res., volume 247, pages 217–222 (1993)] or by heating uronic acid such as glucuronic acid, uronic acid derivative such as glucuronolactone or a substance containing the same (refer to PCT/JP97/03052). In the present invention, it is also possible to use such a heated product or partially purified product or purified product thereof.

For example, when D-glucuronic acid is used as a uronic acid and its 1% solution is heated at 121° C. for four hours, the cyclopentenone is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated, the cyclopentenone is extracted with chloroform from the concentrate and the extract of the concentrate is subjected to a normal phase column chromatography whereupon the cyclopentenone in the heat-treated substance is isolated.

Physical property of the cyclopentenone will be given as hereunder. Incidentally, a mass spectrometric analysis of the cyclopentenone was conducted using a mass spectrometer DX302 (manufactured by Nippon Denshi). Further, measurement of an NMR using heavy chloroform as a solvent was conducted by JNM-A 500 (manufactured by Nippon Denshi). Specific rotation was measured by a DIP-370 polarimeter (manufactured by Nippon Bunko); ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu).

MS m/z 115 [M+H]$^+$ $^1$H-NMR (CDCl$_3$):δ4.20 (1H, d, J=2.4 Hz, 5-H), 4.83 (1H,m, 4-H),6.30 (1H, dd, J=1.2, 6.1 Hz,2-H), 7.48 (1H, dd, J=2.1, 6.1 Hz, 3-H).

Incidentally, the chemical shift value of the $^1$H-NMR was given on a basis that the chemical shift value of CHCl$_3$ was 7.26 ppm.

Optical rotation: $[\alpha]_D^{20}$ 0° (c1.3, water)

UV:$\lambda_{max}$ 215 nm (water)

IR (KBrmethod): absorptions were noted at 3400, 1715, 1630, 1115, 1060, 1025 cm$^{-1.}$ When the isolated cyclopentenone is subjected to an optical resolution, (−)-4,5-dihydroxy-2-cyclopenten-1-one and (+)-4,5-dihydroxy-2-cyclopenten-1-one are obtained. It goes without saying that the cyclopentenone obtained by a synthetic method can be subjected to an optical resolution as well.

For example, the cyclopentenone is dissolved in ethanol. To this ethanolic solution is further added hexane/ethanol (94/6) to prepare a cyclopentenone solution. The cyclopentenone can be optically resolved when this sample solution is subjected to an HPLC using, for example, a Chiral Pack AS (manufactured by Daicel Chemical Industries) under such a condition that the column temperature was 40° C. and the mobile phase was hexane/ethanol (94/6).

Optical rotation of the optically resolved (−)-trans-4,5-dihydroxy-2-cyclopenten-1-one [hereinafter, referred to as (−)-cyclopentenone] is $[\alpha]_D^{20}$-105° (c0.30, ethanol) while that of the optically resolved (+)-trans-4,5-dihydroxy-2-cyclopenten-1-one [hereinafter, referred to as (+)-cyclopentenone] is $[\alpha]_D^{20}$ +104° (c0.53, ethanol). Incidentally, the optical rotation was measured by the above-mentioned polarimeter of the type DIP-370 (manufactured by Nippon Bunko).

After that, each of (−)-cyclopentenone and (+)-cyclopentenone was subjected to structural analysis by means of mass analysis and nuclear magnetic resonance (NMR), measurement of UV absorption spectrum and measurement of infrared absorption spectrum by the method mentioned already. As a result, both optically active substances showed the same result as that of the cyclopentenone before the optical resolution.

Each of the optically resolved (−)-cyclopentenone and (+)-cyclopentenone was converted to a p-dimethylaminobenzoyl derivative, the circular dichroism spectrum (CD) was measured using a circular dichroism dispersimeter of type J-720 (manufactured by Nippon Bunko) and the result was applied to a dibenzoate chirality rule [J. Am. Chem. Soc., volume 91, pages 3989–3991 (1969)] to determine the configuration.

Figure 13:
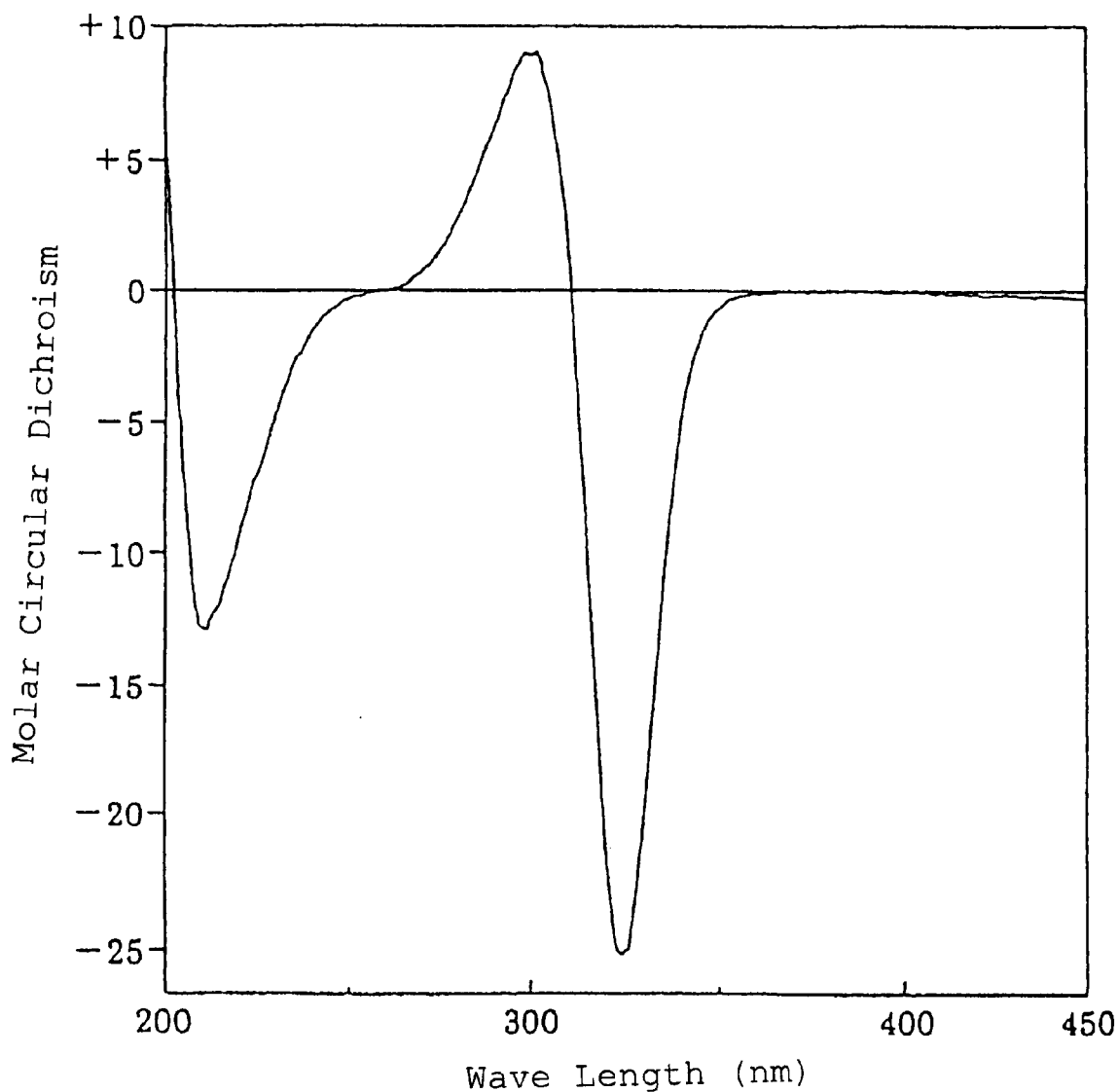
FIG. 13 shows a CD of p-dimethylaminobenzoyl derivative of (−)-cyclopentenone and a stereostructure of (−)-cyclopentenone.
Figure 13:
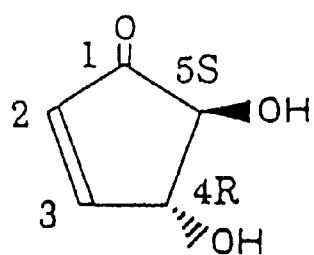

CD of p-dimethylaminobenzoyl derivative of (−)-cyclopentanone and stereostructure of (−)-cyclopentenone are shown in FIG. 13. In the drawing, the ordinate indicates molar circular dichroism while the abscissa indicates wave length (nm). Incidentally, the above stereostructure is given hereunder as the formula [II]

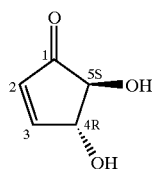

[II]

Figure 14:
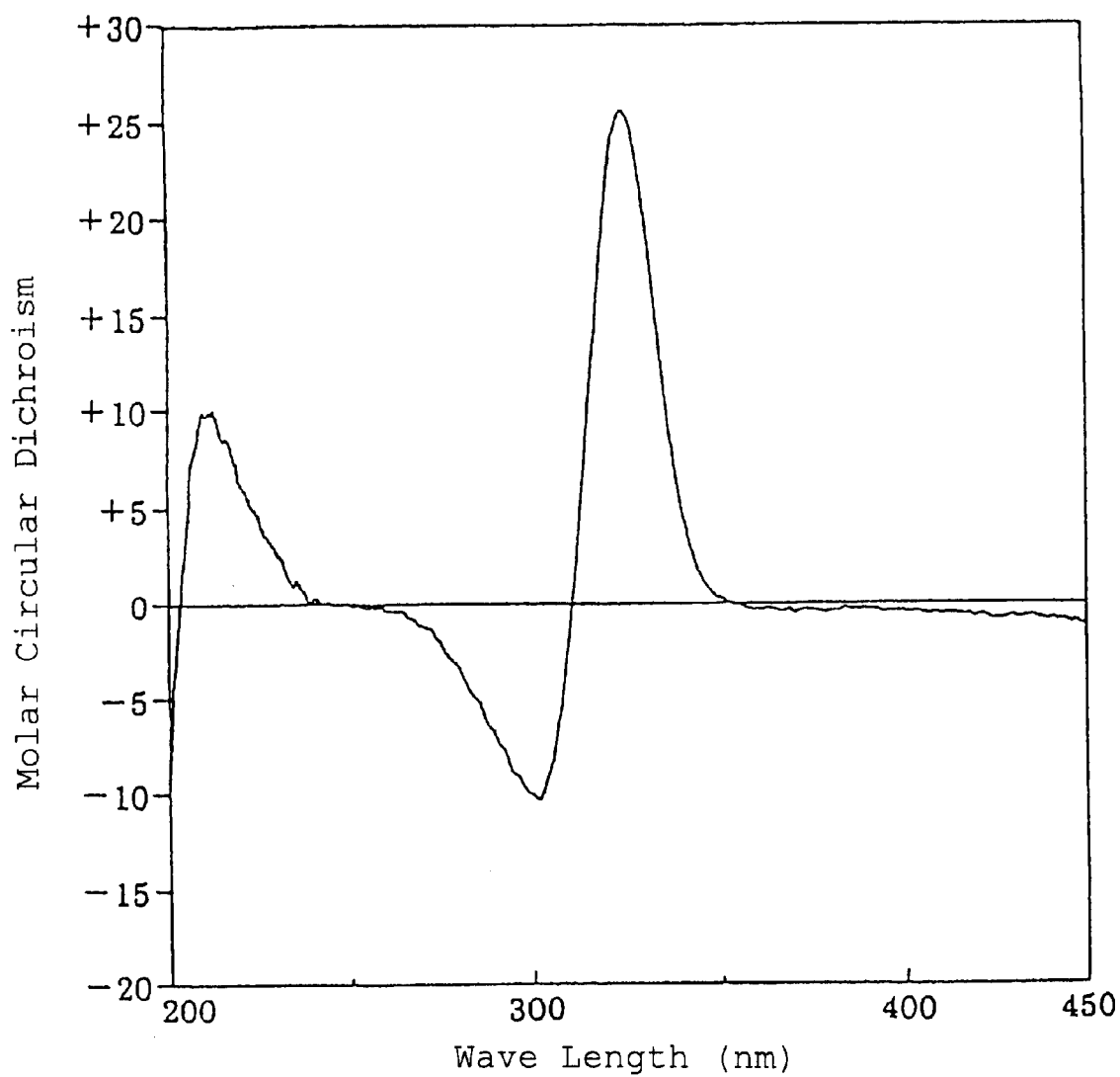
FIG. 14 shows a CD of p-dimethylaminobenzoyl derivative of (+)-cyclopentenone and a stereostructure of (+)-cyclopentenone.
Figure 14:
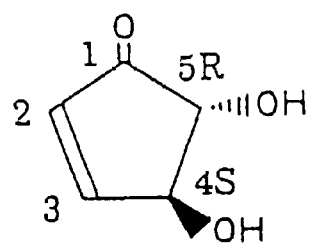

CD of p-dimethylaminobenzoyl derivative of (+)-cyclopentanone and stereostructure of (+)-cyclopentenone are shown in FIG. 14. In the drawing, the ordinate indicates molar circular dichroism while the abscissa indicates wave length (nm). Incidentally, the above stereostructure is given hereunder as the formula [III]

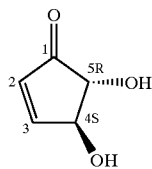

[III]

As shown in FIG. 13, FIG. 14, formula [II] and formula [III], the (−)-cyclopentenone is (−)-(4R,5S)-trans-4,5- dihydroxy-2-cyclopenten-1-one while the (+)-cyclopentenone is (+)-(4S,5R)-trans-4,5-dihydroxy-2-cyclopenten-1-one.

The above-mentioned cyclopentenones or an optically active substance thereof may be manufactured by any method, i.e. they may be manufactured by a method disclosed in this specification or by means of chemical synthesis; and trans- and cis-cyclopentenone or a mixture thereof and an optically active substance thereof may be used in the present invention as well.

Examples of the salt of the cyclopentenone or optically active substance thereof are pharmaceutically acceptable salts and they may be prepared by known converting methods.

The cyclopentenone reacts, for example, with an SH-containing compound (such as cysteine and glutathione) in vivo to produce a metabolic derivative which is useful as a drug. Therefore, it is believed that the pharmaceutical effect of the metabolic derivative is achieved even when the cyclopentenone is administered as well. The reaction product of the cyclopentenone with an SH-containing compound in vivo is presumed to be one of the metabolically effective substances.

Thus, when exemplification is done for an SH-containing compound (R-SH), it reacts with the SH-containing compound to give a compound represented, for example, by the following formula [IV] or [V]. In addition, a compound represented by the formula [V] is converted to a compound represented by the formula [IV].

As such, the cyclopentenone is converted to each of the metabolic derivatives in the presence of an SH-containing compound (R-SH) and such a metabolic derivative produced in vivo achieves an effect as a drug too.

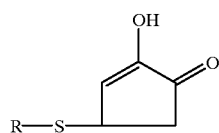

[IV]

(R is a residual group where an SH group is removed from the SH-containing compound.)

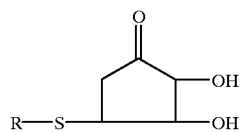

[V]

(R is a residual group where an SH group is removed from the SN-containing compound.)

Accordingly, the use of the cyclopentenone, its optically active substance or salt thereof having an object of production of such a reaction product in vivo, i. e. a metabolic derivative, is covered by the present invention as well.

The cyclopentenone, its optically active substances or salts thereof are the compounds having a physiological action such as antirheumatic action and inhibition action to chronic articular rheumatism. When at least one compound selected from the cyclopentenone, its optically active substance or salt thereof is used as an effective component and is made into a pharmaceutical preparation by combining with known pharmaceutical carriers, it is now possible to prepare an antirheumatic agent. Generally, at least one of the compound selected from the cyclopentenone, its optically active substance or salt thereof is compounded with a pharmaceutically acceptable liquid or solid carrier and, if necessary, solvent, dispersing agent, emulsifier, buffer, stabilizer, filler, binder, disintegrating agent, lubricant, etc. are added thereto to give said pharmaceutical preparation which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where at least one of the compound selected from the cyclopentenone, its optically active substance or salt thereof which is an effective component of the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The antirheumatic agent of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

The dose of the antirheumatic agent is not particularly specified but may be appropriately determined depending upon the dosage form, administration method, purpose of the use and age, body weight, conditions, etc. of the patient. Usually, however, the amount of at least one of the compound selected from the cyclopentenone, its optically active substance or salt thereof contained in the preparation for an adult is 0.1 μg −200 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent maybe taken daily after adding to common food and/or beverage as well.

In addition to above-mentioned antirheumatic activity and inhibition activity to chronic articular rheumatism, the cyclopentenone, its optically active substance or salt thereof has various physiological activity such as anti-inflammatory activity to arthritis, etc., inhibition activity of carrageenan edema, inhibition activity of tumor necrosis factor production, increasing activity of interleukin-10 production, inhibition activity of nitrogen monoxide production, apoptosis-inducing activity to synovial cells, induction activity of Fas antigen production, immunomodulating activity such as inhibition activity of delayed type hypersensitivity, inhibition activity of lymphocyte proliferation, inhibition activity to mixed lymphocyte reaction, inhibition activity to IgE production, inhibition activity to topoisomerase, etc. Thus, the pharmaceutical agent such as anti-inflammatory agent or inflammation preventer, inhibitor of tumor necrosis factor production or preventer of tumor necrosis factor production, enhancer of interleukin-10 production, inhibitor of nitrogen monoxide production, inducer of Fas antigen production, immunomodulator, inhibitor of IgE production, inhibitor of delayed type hypersensitivity and inhibitor of topoisomerase containing at least one compound selected from the cyclopentenone, its optically active substance or salt thereof can be made into pharmaceutical preparations by the same manner as in the case of the above antirheumatic agent and can be administered by the same manner as the above antirheumatic agent.

The dose of those preparations may be appropriately determined depending upon the above antirheumatic agent. For example, in the case of anti-inflammatory agent and an inhibitor of tumor necrosis factor production, the amount of one or more compounds selected from the cyclopentenone, its optically active substances or salts thereof contained in the preparation is preferably 10 pg–50 mg/kg per day for adult while, in the case of inhibitor of nitrogen monoxide production, the amount of one or more compounds selected from the cyclopentenone, its optically active substances or salts thereof contained in the preparation is preferably 0.1 $\mu$g–20 mg/kg per day for adult. Depending upon the object of use, the amount of the effective component in the preparation may be controlled. These agents may be administered orally as it is and, further, the agent may be taken daily after adding to common food and/or beverage as well.

Rheumatism is an autoimmune disease where hindrance takes place in perisoteal cells and cartilage cells and the antiallergic agent of the present invention is useful as a therapeutic agent to autoimmune diseases as well.

The cyclopentenone, its optically active substance or salt thereof inhibits the production of tumor necrosis factor which is believed to directly cause the inflammation in organ-specific autoimmune diseases such as chronic rheumatoid arthritis or inflammatory diseases and enhances the production of interleukin-10 which is a Th1 inhibiting cytokine. Accordingly, symptoms of inflammation such as rheumatism which is an organ-specific autoimmune disease, particularly chronic rheumatoid arthritis are improved; inflammation markers such as C-reactive protein (CRP) value, rheumatoid factor (RF) value and erythrocyte sedimentation rate (blood sedimentation) are greatly decreased; and complications such as dysbasia is significantly improved as well.

Tumor necrosis factor was found as a factor which induces hemorrhagic necrosis to tumor site and, at present, it is recognized as cytokine which broadly participates in inflammatory-based biophylaxis and immune function. Failure in a regulation of production of this tumor necrosis factor causes various inconveniences to the host, and excess or unmodulated production of tumor necrosis factor is related to many diseases including chronic rheumatoid arthritis, rheumatic myelitis, osteoarthritis, gouty arthritis, sepsis, septic shock, endotoxin shock, sepsis by gram-negative bacteria, toxic shock syndrome, cerebral malaria, chronic pneumonia, graft versus host disease, rejection reaction to allograft and other fever and muscular pain by infectious diseases such as influenza, secondary cachexia to infection or malignant tumor, secondary cachexia to human acquired immunodeficiency syndrome (AIDS), AIDS, AIDS-related syndrome, keloid formation, ulcerative colitis, multiple sclerosis, autoimmune diabetes mellitus and systemic lupus erythematosus [Molecular Medicine, volume 33, pages 1010–1020 and pages 1182–1189 (1996)]. The antirheumatic agent of the present invention is useful for therapy of diseases which is mediated or worsened by tumor necrosis factor. The present invention further offers a method for controlling the production of tumor necrosis factor where at least one compound selected from the cyclopentenone, its optically active substance or salt thereof is used as an effective component. The present invention furthermore offers food or beverage containing at least one compound selected from the cyclopentenone, its optically active substance or salt thereof which improves the symptom of the disease or which prevents the disease mediated or worsened by tumor necrosis factor.

Nitrogen monoxide (hereinafter, abbreviated as NO) is a main factor of endothelium-dependent relaxing factor (EDRF) [Nature, volume 327, pages 524–526 (1987)]. The present invention offers a pharmaceutical agent containing at least one compound selected from the cyclopentenone, its optically active substance or salt thereof as an effective component for the therapy or prevention of the diseases requiring the inhibition of NO production. There is no particular limitation for the diseases which require the inhibition of NO production and the examples thereof are systemic hypotension caused by toxic shock or by therapy of certain cytokine, lowering in blood pressure response, autoimmune diseases, inflammation, arthritis, rheumatic arthritis, diabetes mellitus, inflammatory intestine diseases, insufficiency of blood vessel function, etiological dilation of blood vessel, damage of tissues, cardiovascular ischemia, sensitivity to pain, cerebral ischemia, diseases caused by angiogenesis, cancer, etc. The diseases include those which are mentioned in the Japanese Laid-Open Patent Publications Hei-09/504,524; 09/505,288; 08/501,069; 08/512,318; and 06/508,849.

The inhibitor of NO production containing at least one compound selected from the cyclopentenone, its optically active substance or salt thereof as an effective component is useful for the study of mechanism of NO production and of mechanism of biological activity of NO and, in addition, it may be used for screening the substances participating in the mechanism of NO production.

The cyclopentenone, its optically active substance or salt thereof has an inhibition activity of NO production in the NO-productive cells. For example, when endotoxin (lipopolysaccharide or LPS) is added to macrophage cell strain, inducible NO synthetase (NOS) is expressed and NO is secreted into a medium while, when LPS is added in the co-existance of the cyclopentenone, cyclopentenone derivatives or its optically active substances, production of NO is inhibited. When NO production is induced by treating with LPS, survival rate of cells decreases due to a cytopathy activity of NO but, when the cyclopentenone, its optically active substance or salt thereof is added during the treatment with LPS, production of NO decreases and disturbance to cells suppresses as well.

Angiogenesis is essential for growth of solid carcinoma and angioendothelial growth factor/vascular endothelial growth factor (VEGF) plays an important role in this step. In various cancer cells, VEGF is induced by NO. When the cyclopentenone, its optically active substance or salt thereof inhibits the NO production, VEGF production of cancer cells is inhibited as well and, as a result, angiogenesis around the cancer tissues is inhibited. When the cyclopentenone, its optically active substance or salt thereof is administered to mouse wherein solid cancer is formed by a subcutaneous transplantation of cancer cells, formation of blood vessel around the cancer tissues becomes insufficient and cancer is detached therefrom.

Nitrosoamines are a series of compounds which is synthesized by nitroso group addition to secondary amine and several hundreds of nitrosoamines have been known. Many of them damage the DNA, and have carcinogenicity to animals. It has been said that nitrosoamines are greatly related to cancer generation in human being as well and are usually produced in stomach by the reaction of nitrite with amine. Even under a physiological condition of neutral pH, NO reacts with amine to afford nitrosoamine. In addition, NO production is increased in the patients infected by oriental liver fluke and those suffering from hepatic cirrhosis which is highly related to cancer immunologically. Accordingly, when increase of the NO production is suppressed by administration of the cyclopentenone, its optically active substance or salt thereof, it is possible to prevent the generation of cancer, especially in a high-risk group. As such, the cyclopentenone, its optically active substance or salt thereof exhibits an anticancer action in the two steps of inhibition of carcinogenesis and also of inhibition of angiogenesis in cancer tissues.

Further, NO induces the edema which is noted characteristically in inflammatory lesions, i.e. blood vessel permeability [Maeda, et al., Japanese Journal of Cancer Research, volume 85, pages 331–334 (1994)] and also induces the biosynthesis of prostaglandins which are inflammation mediators [Salvemini, et al., Proceedings of National Academy of Sciences, U.S.A., volume 90, pages 7240–7244 (1993)]. On the other hand, it is believed that NO quickly reacts with superoxide radicals and the resulting peroxy nitrite causes inflammatory cells and tissue damages.

When activated immune cells are taken in organ and cytokine is released therefrom, production of NO is induced. Insulin-dependent diabetes mellitus is a diseases caused by a specific destruction of Langerhans β cells and the destruction is done by NO. In addition, the joint fluid of lesions of patients suffering from chronic articular rheumatism, osteoarticular rheumatism, gouty arthritis and arthritis accompanied by Behget disease contains higher concentrations of NO as compared with the joint fluid in the normal joints of such patients or in the joints of healthy persons. When the cyclopentenone, its optically active substance or salt thereof is administered to such patients, production of NO in the lesions is inhibited and the symptom is improved.

During cerebral ischemia and after re-perfusion, production of NO increases and, as a result, cerebral tissues are damaged. When the cyclopentenone, its optically active substance or salt thereof is administered to the patient during cerebral ischemia, damage of the cerebral tissues is reduced and prognosis is improved.

Cell surface antigen which is called as Fas antigen (APO-1 antigen or CD95) has been receiving attention as molecules for inducing the apoptosis [Cell, volume 66, pages 233–243 (1991); J. Exp. Med., volume 169, pages 1747–1756 (1989); J. Biol. Chem., volume 267, pages 10709–10715 (1992); and J. Immunology, volume 184, pages 1274–1279 (1992)].

Fas antigen is expressed in immune cells such as thymus cells, T cells, cytotoxic T cells, B cells and NK cells. Against invasion of foreign non-autoantigen, immune system induces immunoreaction whereby the non-autoantigen is excluded. However, it does not show immunoreaction against autoantigen and self tolerance is established. This is because lymphocytic stem cells having autoreactivity is subjected to removal of clones which is a negative selection whereby the exclusion takes place by death of cells byapoptosis. However, when those cells are not subjected to apoptosis due to some abnormality in living body such as genetic deficiency of Fas antigen, the autoreactive T cells for example are accumulated in peripheral areas. In normal living body, self tolerance is available even for B cells which are the cells in charge of immune and those autoreactive B cells are usually dead due to apoptosis but, when the autoreactive B cells are not subjected to apoptosis due to abnormality such as genetic deficiency of Fas antigen, the autoreactive B cells are accumulated in peripheral areas. In addition, in the case of articular rheumatism, the above-mentioned abnormality in autoreactive lympocytes and abnormality in turn-over of synovial cells are some of the causes of the diseases.

An inducer for production of Fas antigen in which at least one compound selected from the cyclopentenone, its optically active substance or salt thereof is an effective component is useful for induction of apoptosis of unnecessary cells for constituting the living body which are not discharged from living body due to abnormality of turnover and autoreactive lymphocytes and can be used in a method of inducing the Fas antigen production. The agent containing at least one compound selected from the cyclopentenone, its optically active substance or salt thereof as an effective component is also useful as an agent for prevention or therapy of the diseases accompanied by abnormal production of Fas antigen. In the present invention, there is no particular limitation for the diseases accompanied by abnormal production of Fas antigen and its examples are articular rheumatism and autoimmune diseases caused by autoreactive T cells and autoreactive B cells, etc. including the diseases mentioned in the specification of W097/0965.

The cyclopentenone, its optically active substance or salt thereof has an immunomodulating activity such as enhancer activity of interleukin-10 production, inhibition activity of delayed type hypersensitivity reaction, inhibition activity of lymphocyte proliferation, inhibition activity of mixed lymphocyte reaction, inhibition activity of IgE production and inhibition activity of carrageenan edema and the immunomodulator containing at least one compound selected from the cyclopentenone, its optically active substance or salt thereof as an effective component is useful as an agent for therapy or prevention of the diseases caused by abnormality of those immune system and immune factor.

Thus, as a result of reduction of interleukin-10 production, Th1 is activated and inflammation of Th1-dominant autoimmune is induced. This inflammation participates in organ-specific autoimmune diseases such as nephritis and hepatitis as well as graft rejection and allergic contact dermatitis. The above immunomodulator enhances the interleukin-10 production and inhibits the Th1 activity whereby it is useful for the therapy and prevention of those diseases.

Lymphocyte proliferation is a reaction in which mitogen is bonded to the receptor on the surface of lymphocyte to activate the lymphocyte whereby division and growth thereof are promoted. Mixed lymphocyte reaction is a reaction in which lymphocytes obtained from animals of the same species but different strain are subjected to a mixed culture whereupon activation of lymphocytes due to disagreement of main tissue-adaptable antigens is induced and division and growth of the lymphocytes are promoted. The above-mentioned immunomodulator inhibits those reactions and is particularly useful for therapy or prevention of the chronic autoimmune diseases caused by abnormal promotion of lymphocytes such as chronic nephritis, chronic colitis, diabetes mellitus of type I and chronic articular rheumatism and is also useful in inhibiting the graft rejection.

Carrageenan-induced pedel edema model is a reaction in which carrageenan which is an inflammation inducer is subcutaneously injected to paws to induce inflammation cells such as macrophage and neutrophils whereby blood vessel permeability is enhanced by inflammatory factors produced from those cells inducing the edema. The inhibiting action of the above-mentioned immunomodulator to edema is useful for therapy or prevention of diseases requiring control of enhancement of blood vessel permeability such as chronic articular rheumatism.

In allergic diseases represented by asthma and atopic dermatitis, release of chemical mediators from mast cells plays an important role in allergic reaction. This reaction is induced when IgE is bonded to receptors on cell membrane to form a cross-linkage and the above immunomodulator inhibits the production of IgE and is quite useful for improvement of symptoms and/or prevention of diseases mediated or worsened by the IgE production such as allergic diseases caused by IgE including bronchial asthma, allergic rhinitis, atopic dermatitis, allergic conjunctivitis, urticaria, anaphylactic shock, etc. In addition, the above immunomodulator inhibits the delayed type hypersensitivity reaction and is useful for therapy and prevention of the diseases accompanied by the delayed type hypersensitivity such as contact hypersensitivity, allergic contact dermatitis, bacterial allergy, fungal allergy, viral allergy, drug allergy, thyroiditis and allergic encephalitis.

In the present invention, the cyclopentenone, its optically active substances or salt thereof and a material selected from heat-treated product of the cyclopentenone and a partially purified cyclopentenone from said heat-treated product are used to offer functional food or beverage having antirheumatic activity, anti-inflammatory activity, inhibition activity of tumor necrosis factor production, increasing activity of interleukin-10 production, inhibition activity of nitrogen monoxide production, apoptosis-inducing activity to synovial cells, induction activity of Fas antigen production, immunomodulating activity such as inhibition activity of delayed type hypersensitivity, inhibition activity of lymphocyte proliferation, inhibition activity to mixed lymphocyte reaction, inhibition activity to IgE production and inhibition activity to topoisomerase such as food or beverage for improving rheumatism, food or beverage for improving inflammation, food or beverage for inhibiting the tumor necrosis factor production, food or beverage for enhancing interleukin-10 production, food or beverage for inhibiting nitrogen monoxide production, food or beverage for inducing Fas antigen production, food or beverage for immunomodulation, food or beverage for inhibiting IgE production and food or beverage for topoisomerase inhibition.

There is no particular limitation for the method of manufacturing food or beverage of the present invention but cooking, processing and commonly-used manufacturing methods for food or beverage may be applied provided that at least one compound selected from the cyclopentenone, an optically active substance or a salt thereof having a physiological action such as an antirheumatic action is contained in the resulting food or beverage as an effective component. Food or beverage where one or more compounds selected from the cyclopentenone, its optically active substances or salts thereof is/are contained therein, added thereto and/or diluted therein is defined as the food or beverage of the present invention.

There is no particular limitation for the shape of food or beverage of the present invention so far as at least one compound selected from the cyclopentenone, an optically active substance or a salt thereof is contained therein, added thereto and/or diluted therein as an effective component. Thus, the shape includes the ones which can be orally taken such as tablets, granules, capsules, gel and sol.

Due to the food or beverage of the present invention having physiological activities of at least one or more compounds selected from the cyclopentenone, its optically active substances or salts thereof such as antirheumatic activity, anti-inflammatory activity, inhibition activity of tumor necrosis factor production, increasing activity of interleukin-10 production, inhibition activity of nitrogen monoxide production, induction activity of Fas antigen production, immunomodulating activity such as inhibition activity of delayed type hypersensitivity, inhibition activity to IgE production and inhibition activity to topoisomerase, etc., it is a healthy food or beverage having symptom-improving effect to the diseases showing sensitivity to the cyclopentenone, its optically active substance or salt thereof and preventing effect to said diseases, and further, it is food or beverage which is useful for maintaining the consistency of living body.

It is now possible in accordance with the present invention that an appropriate amount of the cyclopentenone, its optically active substance or salt thereof having a physiological activity is contained in food or beverage. Because of the physiological action of those compounds such as apoptosis-inducing activity to synovial cells, induction activity of a Fas antigen production, inhibition activity of the tumor necrosis factor production, inhibition activity of the NO production and activity of improving and/or preventing the symptom of rheumatism, particularly that of chronic articular rheumatism, the food or beverage of the present invention is quite useful for improvement or prevention of symptoms of rheumatism, complication due to rheumatism, difficulty in walking, etc.

No toxicity was observed in the compound used in the present invention even when the dose which is effective to achieve those physiological activities is administered. In the case of oral administration for example, no dead case was observed in rats by a single oral administration of 100 mg/kg of any of the cyclopentenone, an optically active substance or a salt thereof.

EXAMPLES

The present invention will be further illustrated by way of the following examples although the present invention is never limited to those examples. Incidentally, "%" used in the examples stands for "% by weight".

Referential Example 1.

D-Glucuroic acid (G 5269; manufactured by Sigma) (10 g) was dissolved in 1 liter of water, heated at 121° C. for four hours and concentrated in vacuo until about 10 ml. This was mixed with 40 ml of an upper layer of a 3:2:2 mixture of butyl acetate, acetic acid and water and centrifuged and the resulting supernatant liquid was concentrated in vacuo until about 10 ml.

The above extract was applied to silica gel (BW-300SP; 2×28 cm; manufactured by Fuji Silycia) for a column chromatography and separated using an upper layer of a 3:2:2 mixture of butyl acetate, acetic acid and water as an eluate at the flow rate of about 5 ml/minute under a pressure of 0.2 kg/cm$^2$ using a compressor. Fractionation was conducted to make a volume of one fraction 10 ml and a part of each fraction was analyzed by a thin layer chromatography whereupon cyclopentenone of a high purity was contained in 61st to 80th fractions. Those fractions were collected, concentrated in vacuo, extracted with 40 ml of chloroform and the extract was concentrated in vacuo to afford 100 mg of cyclopentenone.

The fraction was separated by means of a normal phase HPLC using a Palpack type S column and, when a detection was conducted by an ultraviolet absorption of 215 nm, the purity was found to be 98%.

The above cyclopentenone (113.9mg) was dissolved in 2.85 ml of ethanol. To this ethanolic solution was added 3.85 ml of hexane/ethanol (94/6) to prepare a cyclopentenone solution (17 mg/ml). This solution was filtered through a filter of 0.5 $\mu$m to prepare a sample solution for an optical resolution HPLC.

This sample solution was applied to an optical resolution HPLC, each of the fractions of the (−)-cyclopentenone in the earlier peak and the (+)-cyclopentenone in the later peak was collected and evaporated to dryness in vacuo to give 43.2 mg of the (−)-cyclopentenone and 43.0 mg of the (+)-cyclopentenone.

Conditions for Optical Resolution HPLC

Columns: Chiral Pack AS (manufactured by Daicel) 2.0 cm×25.0cm

Column temperature: 40° C.

Mobile phase: hexane/ethanol (94/6)

Flow rate: 14.0 ml/minute

Detection: UV 210 nm

Amount of the charged sample: 150 $\mu$l (2.55 mg)

Each of the (−)-cyclopentenone and (+)-cyclopentenone obtained herein contains about 1% of enantiomer and, therefore, they were subjected to an optical resolution under the above-mentioned conditions again. As a result, 19.7 mg of the (−)-cyclopentenone containing no enantiomer was obtained from 30.0 mg of the (−)-cyclopentenone of the earlier peak while, from 37.4 mg of the (+)-cyclopentenone of the later peak, 27.7 mg of the (+)-cyclopentenone containing no enantiomer was obtained. Incidentally, the eluting times in optical resolution HPLC of the (−)-cyclopentenone and (+)-cyclopentenone were 33 minutes and 40 minutes, respectively.

Example 1

When 50 ml (containing 2 mg of the cyclopentenone) per day of the beverage prepared according to Example 12-(2) was given for one month to a female patient (56 years old) who was diagnosed as chronic articular rheumatism five year ago and treated as chronic arthritic rheumatism by means of steroids, antirheumatic agents, sedative anti-inflammatory agents, etc. as therapeutic agents but showed no improvement in symptoms, where CRP value being not less than 3 mg/dl, RF value being not less than 300 U/ml and erythrocyte sedimentation rate being not less than 20 ml/hr and was almost bedridden due to difficulty in walking, hematological improvements in symptoms of chronic articular rheumatism such as CRP data, RF data and erythrocyte sedimentation rate was noted. In addition, kinetic function in daily life such as walking was significantly improved together with decreases in the above data.

Example 2

DSEK cell (cell strain stored at the Department of Second Internal Medicine, Integrated Medical Center, Saitama College of Medicine) which was a fibroblast strain established from synovial membrane of a patient suffering from chronic articular rheumatism was incubated in an Iscob-modified Dulbecco medium (IMDM, manufactured by Gibco, 12440-053) containing 10% fetal bovine serum (FBS, manufactured by Gibco, 26140-079) at 37° C. in the presence of 5% carbon dioxide gas until confluent and then the cells were collected by peeling off with trypsin-EDTA (manufactured by Gicbo, 25300-054). The cells were suspended in the above-mentioned medium until 25,000 cells/ml were resulted and each 100 $\mu$l was placed in each well of a 96-well microtiter plate. After five days from incubation when the state of confluence was almost achieved, the medium was discarded and then the above-mentioned medium containing 2.5, 5, 10, 20 or 30 $\mu$M of cyclopentenone was added. After incubating for 24, 48 or 72 hours, 10 $\mu$l of a premix WST-1 (manufactured by Takara Shuzo, MK400) was added thereto followed by subjecting to a reaction at 37° C. for four hours. The value obtained by deducting the absorbance at 650 nm ($A_{650}$) from that at 450 nm ($A_{450}$) was defined as a degree of growth of cell.

The result is as shown in Table 1.

TABLE 1

| Concentration | $A_{450} - A_{650}$ after | |
|---|---|---|
| ($\mu$M) | 24 hours | 48 hours |
| 0 | 0.846 | 1.270 |
| 2.5 | 0.724 | 0.956 |
| 5 | 0.530 | 0.541 |
| 10 | 0.325 | 0.216 |
| 20 | 0.247 | 0.192 |
| 30 | 0.253 | 0.187 |

In both cases of incubating for 24 hours and 48 hours, cell growth was inhibited in the sections where 5 $\mu$M or more cyclopentenone was added as compared with the control where water was added and, in the section where 10 $\mu$M of cyclopentenone was added, production of apoptic bodies was noted. In the section where 20 $\mu$M or more cyclopentenone was added, living cells were hardly noted.

As such, the cyclopentenone showed apoptosis-inducing action and growth-inhibiting action to synovial cells. (−)-Cyclopentenone and (+)-cyclopentenone showed the similar results as well.

Example 3

(1) $5×10^5$ cells/ml of Jurkat cells (ATCC TIB-152) and Molt-3 cells (ATCC CRL-1552) which were human T cell leukemia cell stain were incubated in an RPMI 1640 medium (manufactured by Gibco BRL) containing 10% fetal calf serum (FCS, manufactured by Bio Whittaker) at 37° C. in the presence of 5% $CO_2$ and 0, 5, 10 or 20 $\mu$M of cyclopentenone was added thereto followed by incubating for another 24 hours. Cell growth was measured by an MTT method [Mosmann, et al.: J. Immunol. Methods, volume 65, pages 55–63 (1983)] wherein degree of cell growth was determined by the absorbance at 560 nm.

The result was that, in both cell strains, cell growth was inhibited to an extent of about 50% and not less than 75% in the sections where 10 $\mu$M and 20 $\mu$M of cyclopentenone were added, respectively as compared with the control where water was added. In case 5 $\mu$M or less cyclopentenone was added, there was no significant effect in the growth of cells.

As such, the cyclopentenone inhibited, in a concentration-dependent manner, the growth of Jurkat cells and Molt-3 cells which were T cell leukemia cell strains.

Figure 2:
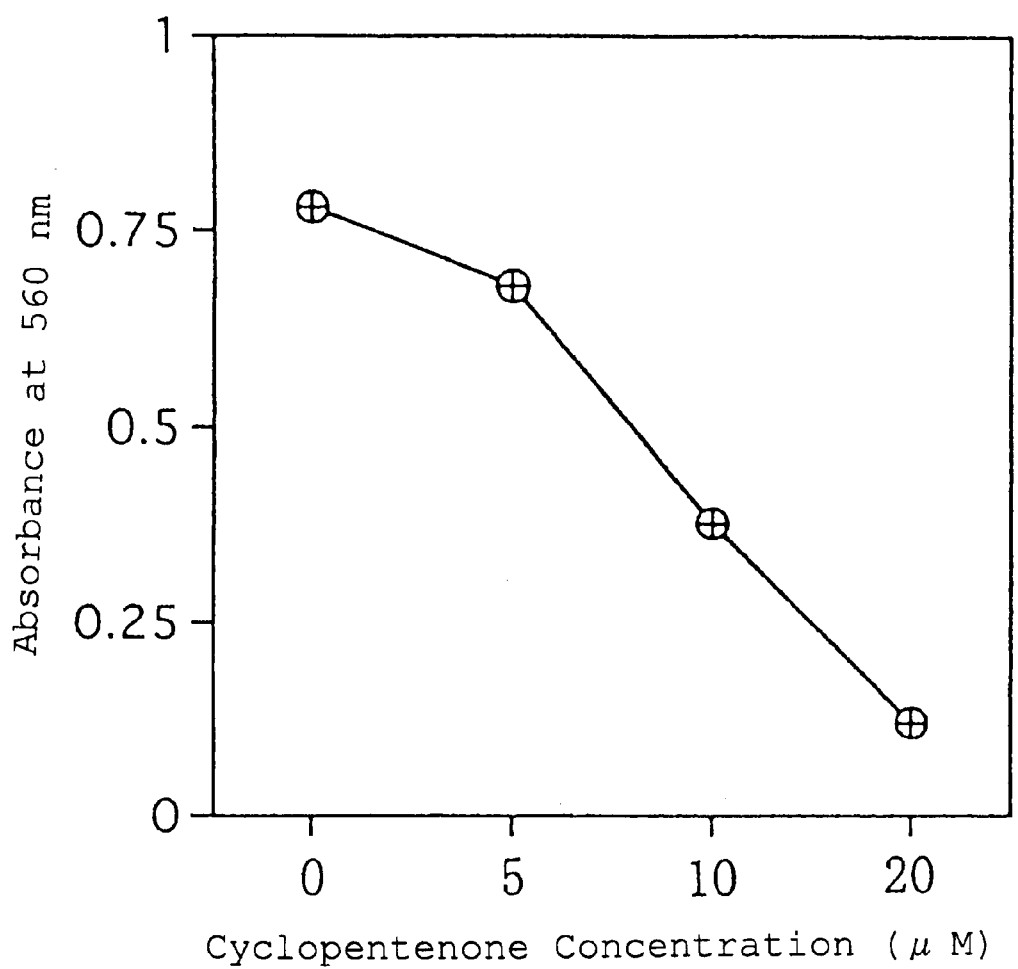
FIG. 2 shows an influence of cyclopentenone on the growth of Molt-3 cells.

The results are given in FIG. 1 and FIG. 2. FIG. 1 shows an influence of cyclopentenone on the growth of Jurkat cells while FIG. 2 shows an influence of cyclopentenone on the growth of Molt-3 cells. In FIG. 1 and FIG. 2, abscissa indicates cyclopentenone concentration ($\mu$M) while ordinate indicates absorbance at 560 nm.

(2) Influence of cyclopentenone on Fas antigen expression (productive induction) in Jurkat cells and Molt-3 cells was measured as follows. In a 10% FCS-containing RPMI 1640 medium containing 0, 1, 5, 10 or 20 $\mu$M of cyclopentenone or GM, 5×10$^5$ cell/ml of Jurkat cells or Molt-3 cells were incubated at 37° C. for 24 hours in the presence of 5% of $CO_2$ and then subjected to a two-step immunostaining using an anti-Fas antibody (manufactured by Boehringer-Ingelheim) in accordance with a method of Munker [Munker, R.: Ann. Hematol., volume 70, pages 15–17 (1995)].

Fluorescence intensity of the stained 1×10$^4$ cells was measured by a flow cytometer (Orthocytron; manufactured by Ortho Diagnostic Systems) and rate of the cell showing a predetermined or higher fluorescence intensity which were Fas antigen-expressing cells was calculated.

The result was that, in both cell strains, the rate of Fas antigen-expressing cells increased on a concentration-dependent manner when 1–20 $\mu$M of cyclopentenone was added.

Figure 3:
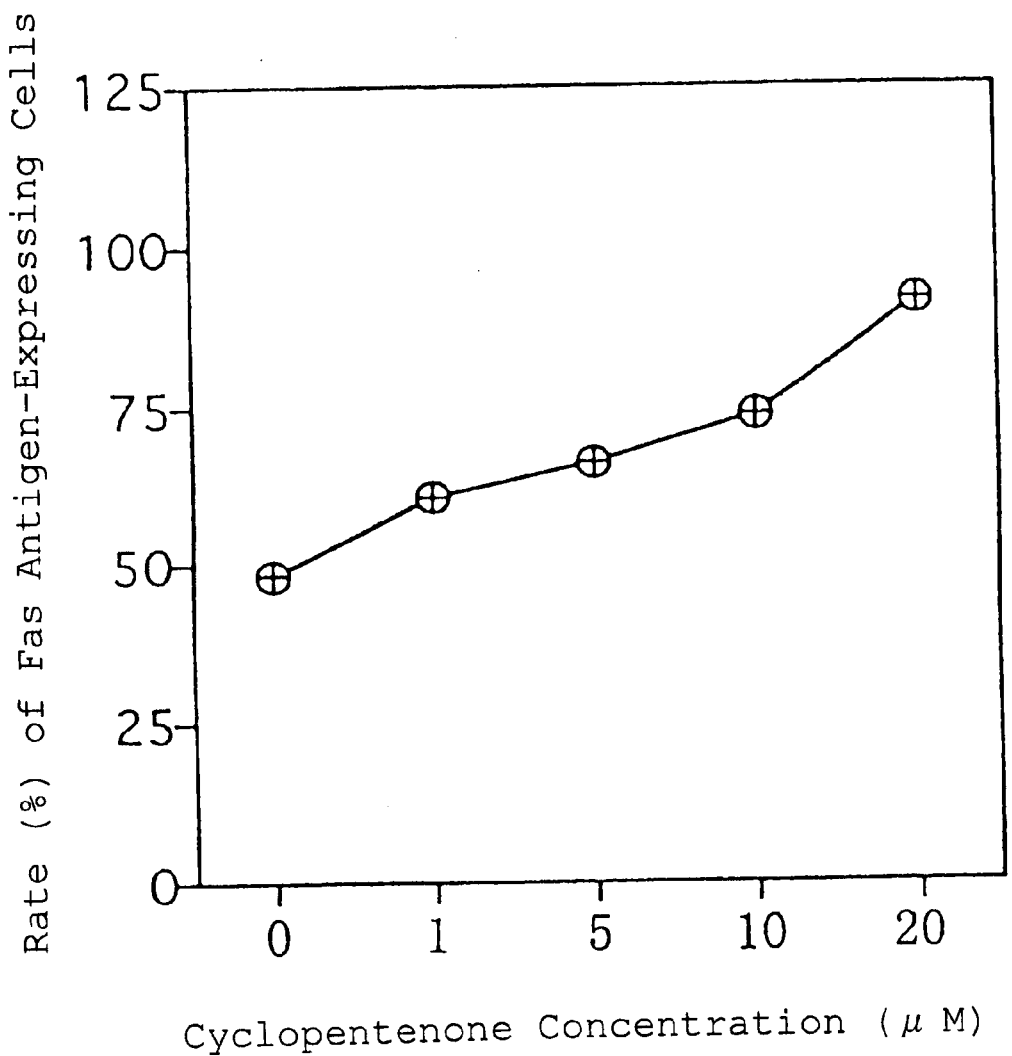
FIG. 3 shows expression of Fas antigen in Molt-3 cells.
Figure 4:
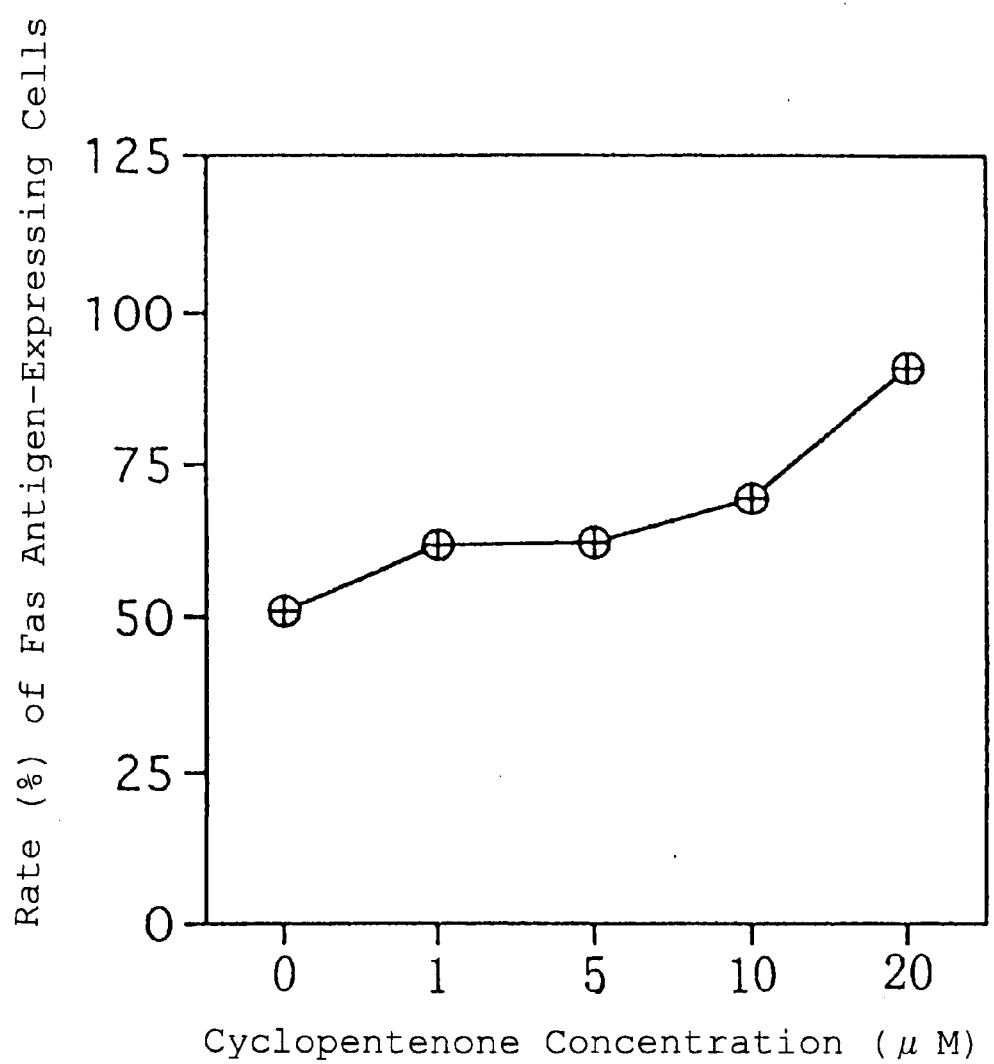
FIG. 4 shows expression of Fas antigen in Jurkat cells.

The results are shown in FIG. 3 and FIG. 4. Thus, FIG. 3 shows the expression of Fas antigen in Molt-3 cells while FIG. 4 shows that in Jurkat cells. In FIG. 3 and FIG. 4, abscissa indicates cyclopentenone concentration ($\mu$M) while ordinate indicates the rate (%) of Fas antigen-expressing cells whereby an action of inducing the Fas antigen production by cyclopentenone was noted.

(3) Molt-3 cells were incubated for 1, 3, 6, 12 or 24 hours after addition of 10 $\mu$M of cyclopentenone and then the rate of the cells which expressed Fas antigen was measured.

The result was that, when 10 $\mu$M of cyclopentenone was added, the rate of the Fas antigen-expressing cells started increasing after an hour from the incubation and gradually continued to increase until 24 hours after the incubation.

Figure 5:
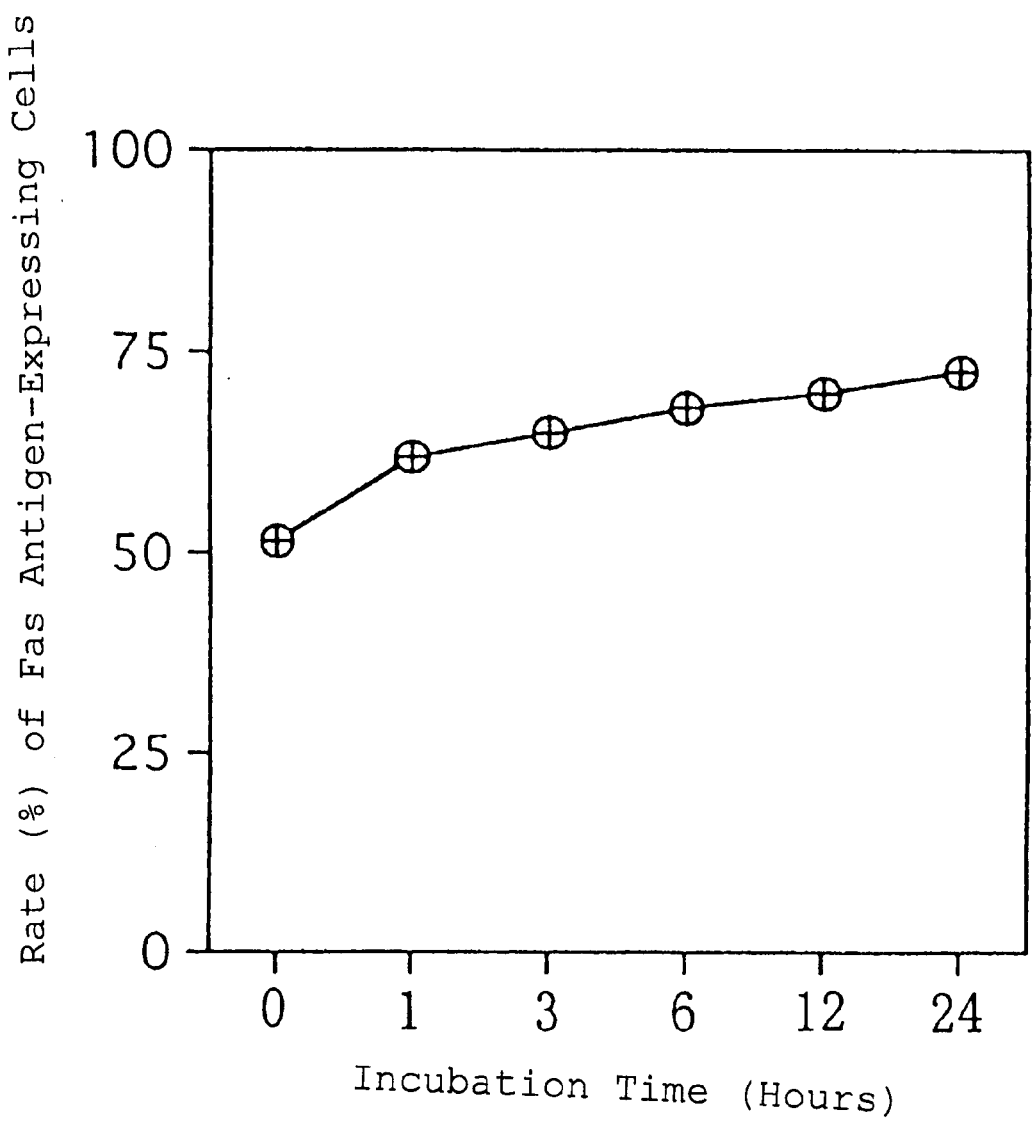
FIG. 5 shows the changes in the rate of Fas antigen expression cells when incubation was conducted after adding 10 μM of cyclopentenone to Molt-3 cells.

The result is shown in FIG. 5. Thus, FIG. 5 shows a change in the rate of Fas antigen-expressing cells when incubation was conducted after adding 10 $\mu$M of cyclopentenone to Molt-3 cells in which abscissa indicates incubation time (hours) while ordinate indicates the rate (%) of Fas antigen-expressing cells.

Thus, as mentioned in Example 3- (1) to (3), an action of cyclopentenone for inducing the expression of Fas antigen was ascertained. (−)-Cyclopentenone and (+)-cyclopentenone gave the similar results as well.

Example 4

Carrageenan-induced pedal edema models which were animal model of chronic articular rheumatism were prepared as follows using male Lewis rats [purchased from Seac-Yoshitomi when five weeks age (body weight: about 130 g) followed by subjecting to a preliminary breeding for one week at our end] and the test drugs were evaluated.

To the rats which were fasted since 18 hours before initiation of the experiment was orally administered with 10 ml/kg of cyclopentenone which was prepared with distilled water (manufactured by Otsuka Pharmaceutical) to make 1 and 5 mg/ml.

After 0.5 hour from administration of the test drug, 100 $\mu$l/rat of 1% suspension of carrageenan (manufactured by Wako) in a physiologically saline solution (manufactured by Otsuka Pharmaceutical) was injected to right paw to induce pedal edema. After three hours from the carrageenan injection, volume of right paw of the rat was measured by a pedal volume measuring device (manufactured by UGO BASILE). Incidentally, the measured value was expressed by calculating the increasing rate from the right paw volume of each rat measured before the carrageenan administration.

Figure 6:
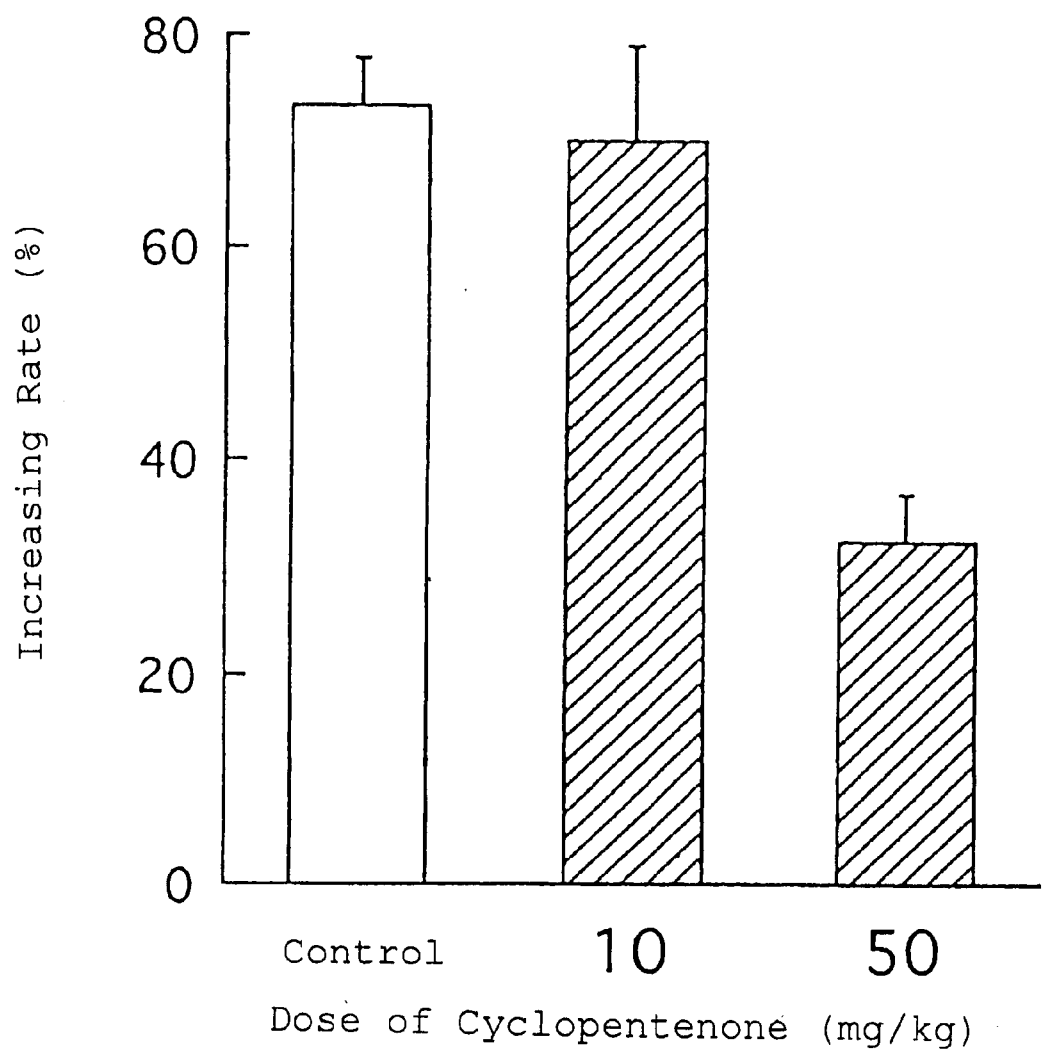
FIG. 6 shows the relation between the amount of the cyclopentenone and the increasing rate of the pedal edema.

The result is shown in FIG. 6. Thus, FIG. 6 shows the relation between the amount of cyclopentenone and the increasing rate of the pedal edema in which ordinate indicates an increasing rate (%) while abscissa indicates a dose of cyclopentenone (mg/kg).

Cyclopentenone showed a significant inhibition activity to pedal edema at the dose of 50 mg/kg. (−)-Cyclopentenone and (+)-cyclopentenone gave the similar effects as well.

Example 5

(1) LPS (lipopolysaccharide; manufactured by Sigma; L-2012) derived from *Salmonella abortus equi* dissolved in a physiological saline solution was intraperitoneally administered (0.1 mg/kg) to female mice of CDF1 strain of 20 weeks age to prepare endotoxin-shock models.

The cyclopentenone was administered either intraperitoneally or orally at a dose of 30 mg/kg at 30 minutes before the administration of LPS. On the other hand, the control group was not administered as such. After 90 minutes from the administration of LPS, blood was collected from the mice and serum was separated. Then the amount of tumor necrosis factor in the serum was measured by means of a TNF-α• ELISA Kit (manufactured by Genzyme) and the effect of inhibiting the tumor necrosis factor production by administration of the cyclopentenone was measured.

The result is given in Table 2. Thus, as compared with the control group, concentrations of tumor necrosis factor in the serum were low in the cyclopentenone-administered groups both in the groups of intraperitoneal and oral administrations whereby production of tumor necrosis factor was significantly suppressed by administration of the cyclopentenone.

TABLE 2

| Groups | Numbers of Mice | TNF-α in Serum (ng/ml) Average ± SE |
|---|---|---|
| Control group | 5 | 3.96 ± 0.52 |
| Cyclopentenone-administered group (intraperitoneal administration) | 5 | 0.58 ± 0.08** |
| Cyclopentenone-administered group (oral administration) | 5 | 1.80 ± 0.30* |

**: having significant difference to control at p < 0.001
*: having significant difference to control at p < 0.01

(2) LPS was intraperitoneally injected (10 $\mu$g/mouse) to female CDF1 mice of eight weeks age and endotoxin-shock models were prepared. The cyclopentenone was subcutaneously administered at the dose of 0.03, 0.3, 3 and 30 mg/kg at fifteen minutes before administration of LPS (each group consisting of four mice). After one hour from the administration of LPS, blood was collected from the mice, serum was separated and amount of the tumor necrosis factor-α in the serum and amount of the interleukin-10 were measured by a commercially available ELISA kit (manufactured by Endogen).

The result is shown in Table 3. Thus, the cyclopentenone suppressed an increase in the concentration of tumor necrosis factor-α in serum by administration of LPS on a dose-dependent manner. Furthermore, as compared with the control group to which distilled water was administered (four mice per one group), concentrations of interleukin-10 in the serum were significantly raised in the cyclopentenone-administered (30 Omg/kg) group.

TABLE 3

|  | Dose (mg/kg) | Tumor Necrosis Factor (ng/ml) Average ± SD | Amount of interleukin-10 in the serum (ng/ml) Average ± SD |
|---|---|---|---|
| Control group | — | 3.00 ± 0.30 | 1.79 ± 0.29 |
| Cyclopentenone-administered group | 30 | 0.24 ± 0.08 | 3.16 ± 0.28 |
|  | 3 | 1.41 ± 0.45 | 1.95 ± 0.20 |
|  | 0.3 | 2.30 ± 0.24 | 1.32 ± 0.16 |
|  | 0.03 | 2.68 ± 0.28 | 1.58 ± 0.29 |

(3) Paraffin oil (Cosmo Bio) (2 ml) was intraperitoneally administered to female CDF1 mice of eight weeks age to induce celiac M ø. After one week from administration of paraffin oil, 4 ml of an RPMI-1640 medium (Gibco) was intraperitoneally infused, well massaged and recovered to give celiac cells.

The celiac cells were washed with an RPMI-1640 medium twice and suspended in an RPMI1640 medium containing 10% of fetal calf serum (FCS; High-Clone) to adjust the cell concentration to $1 \times 10^6$ cells/ml. The cell solution (1 ml) prepared as such was planted on a 24-well plate and incubated in a $CO_2$ incubator at 37° C. for two hours. Non-adhesion cells contained in the supernatant liquid after incubation was removed and the adhesion cells were used as celiac M ø.

To each of the well of the plate was added 800μl of RPMI-1640 medium containing 10% of FCS, then 100μl of 1, 10, 100 and 1000 μM cyclopentenone dissolved in a physiological saline solution (manufactured by Qtsuka Pharmaceutical) was added thereto and incubation was conducted in a $CO_2$ incubator at 37° C. for one hour.

After the incubation, 100μl of 100 ng/ml LPS (manufactured by Sigma) was added and incubation was conducted for 24 hours more. After completion of the incubation, the supernatant liquid was recovered therefrom and the amount of TNF-α produced therein was determined using a commercially available ELISA kit (manufactured by Endogen).

Figure 7:
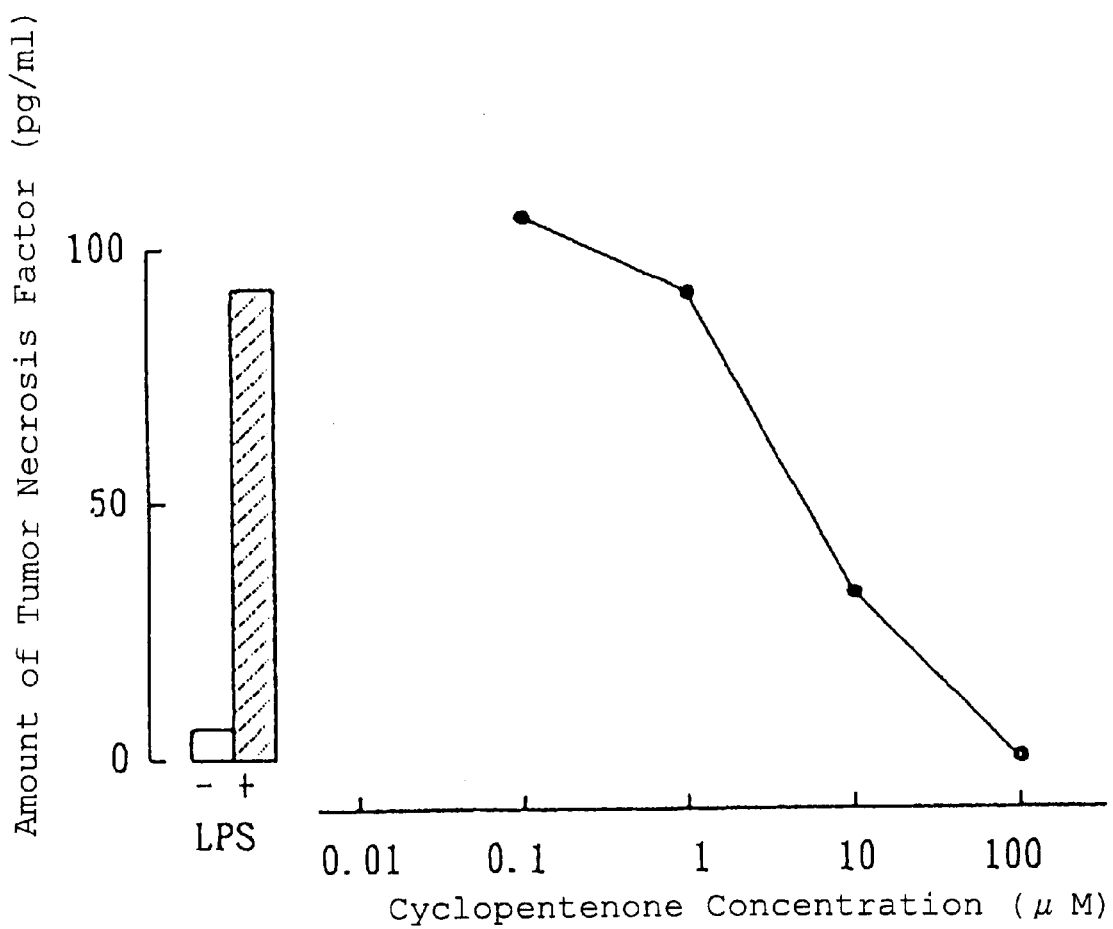
FIG. 7 shows the relation between the amount of the cyclopentenone and the produced amount of tumor necrosis factor.

The result is shown in FIG. 7. Thus, FIG. 7 shows the relation between the concentration of cyclopentenone and the produced amount of tumor necrosis factor in which ordinate indicates amount of tumor necrosis factor (pg/ml) while abscissa indicates cyclopentenone concentration (μM) of each sample.

The cyclopentenone in a concentration of not less than 10 μM significantly inhibited the production of tumor necrosis factor from celiac macrophage of mice induced by LPS.

As shown in the above Example 5-(1) to (3), the cyclopentenone has an inhibition activity of the production of tumor necrosis factor and an increasing activity of interleukin-10 production. (−)-Cyclopentenone and (+) -cyclopentenone showed the same results as well.

Example 6

Inhibition activity of cyclopentenone to NO production and to cell damage was measured as follows using mouse macrophage cell strain RAW264.7 cells (ATCC TIB 71) and LPS.

Dulbecco-modified Eagle's medium (manufactured by Life Technologies Oriental; 11054-020) containing 2 mM of L-glutamine (manufactured by Life Technologies Oriental; 25030-149) containing no Phenol Red containing 5 ml of 10% fetal calf serum (manufactured by Gibco) containing $1.5 \times 10^6$ cells of RAW 264.7 was incubated in a six-well tissue culture plate in the presence of 5% carbon dioxide gas at 37° C. for 12 hours, 50μl of 50 μg/ml LPS (manufactured by Sigma) was added, then each 50μl of 500 μM cyclopentenone, 250 μM cyclopentenone, 100 μM cyclopentenone or 50 μM cyclopentenone was added to each well, incubation was further continued for additional 12 hours and, after that, $NO_2^-$ produced by oxidation of NO in the medium and amount of living cell numbers were measured. Incidentally, a section where no LPS was added and a section where no cyclopentenone was added were prepared as controls.

For the measurement of $NO_2^-$, 100μl of incubated supernatant fluid was separated from each well, 10μl of 50 μg/ml solution of 2,3-diaminonaphthalene (manufactured by Dojindo Laboratories; 341-07021)(a solution in 0.62N hydrochloric acid) was added, there mixture was allowed to stand for 15 minutes, then 5μl of 2.8N aqueous solution of sodium hydroxide was added and the fluorescence of the resulting naphthalene triazole was measured by a Titertec Fluoroscan II (sold by Dainippon Pharmaceutical) at excitation wave length of 355 nm and measuring wave length of 460 nm. All experiments were conducted in two series, a control value of the section to which no LPS was added was deducted from the average value thereof and a comparison was conducted in terms of the relative value of each section to the value of the section to which LPS was added.

The result was that cyclopentenone inhibited the NO production induced by LPS in RAW 264.7 cells and further that it inhibited the cell damage in RAW 264.7 cells caused by LPS.

Figure 8:
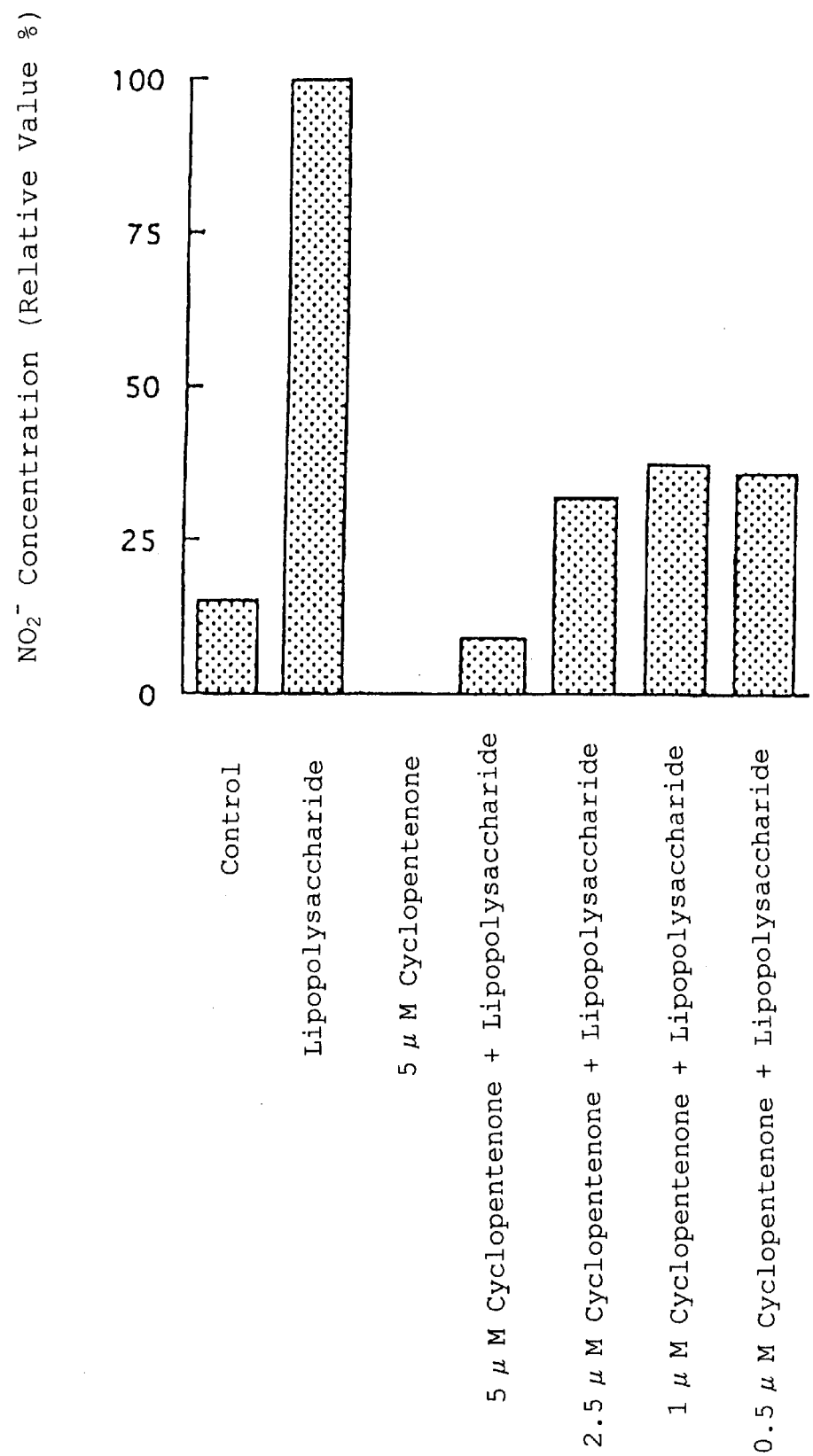
FIG. 8 shows the relation between cyclopentenone concentration and $NO_2^-$ concentration.
Figure 9:
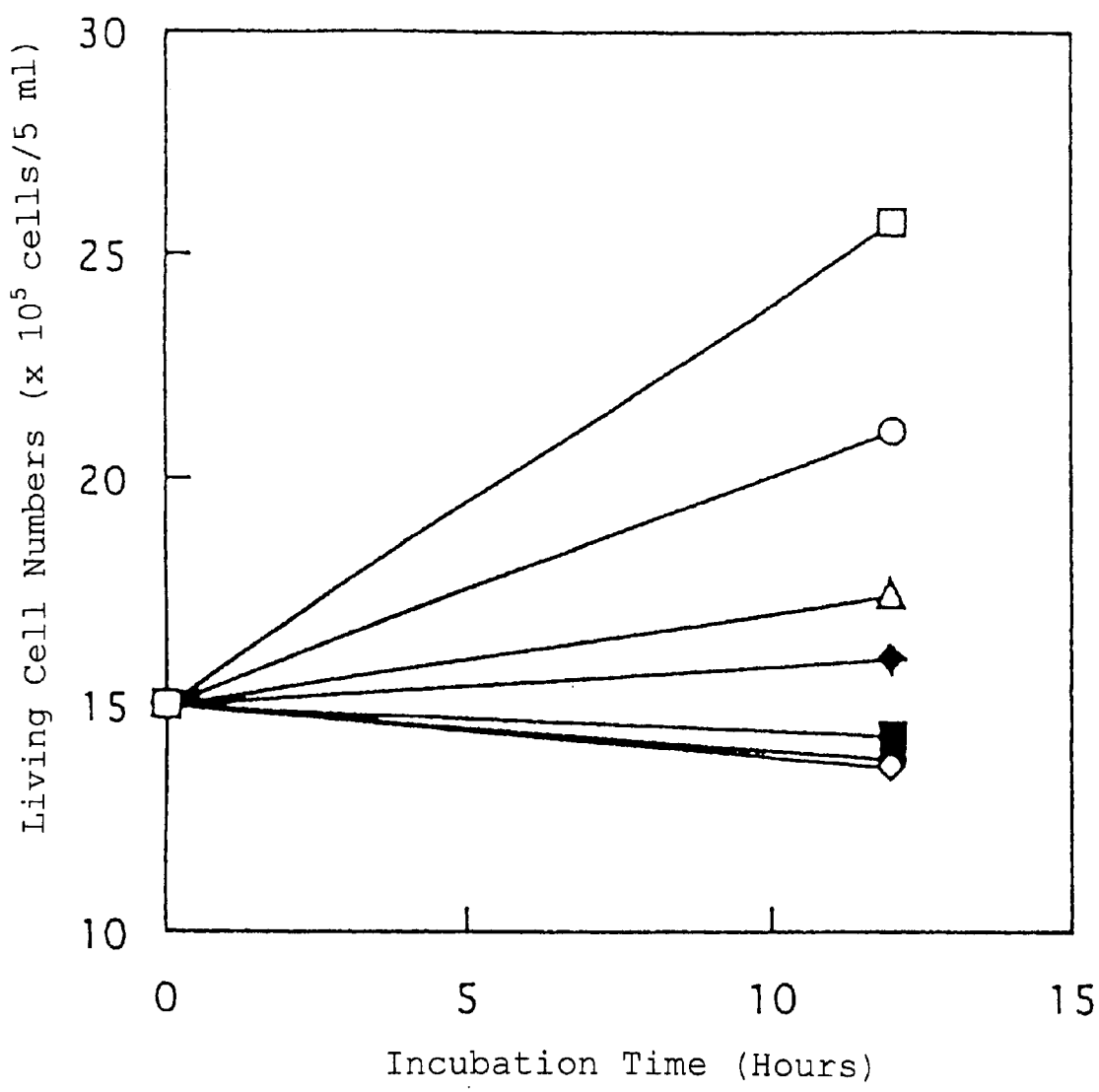
FIG. 9 shows the relation between incubation time and living cell numbers in the presence of the cyclopentenone.

The results are shown in FIG. 8 and in FIG. 9. FIG. 8 shows the relation between the cyclopentenone concentration and $NO_2^-$ concentration in the culture liquid in which ordinate indicates a relative value (%) of the $NO_2^-$ concentration. FIG. 9 shows the relation between the incubation time and living cell numbers in the presence of cyclopentenone in which ordinate is living cell numbers ($\times 10^5$ cells/5 ml) contained in 5 ml of the culture liquid while abscissa indicates an incubation time (hours). In FIG. 9, open square (□) indicates control; open rhomb (◇) indicates LPS; open circle (○) indicates 5 μM cyclopentenone; open triangle (Δ) indicates the case 5 μM cyclopentenone +LPS; black square (■) indicates 2.5 μM cyclopentenone +LPS; black rhomb (◆) indicates 1 μM cyclopentenone +LPS; and black circle (●) indicates 0.5 μM cyclopentenone +LPS.

As such, the cyclopentenone showed an inhibiting action to the NO production. (−)-Cyclopentenone and (+) -cyclopentenone showed the similar effects as well.

Example 7

(1) BALB/c male mice (Nippon Clare) (five weeks age; five mice per group) were sensitized by intraperitoneal administration of 100μl of 0.01% physiological saline solution of egg white albumin (Sigma) and 100μl of alum (trade name: Imject Alum; Pearce) and, 11 days thereafter, peripheral blood was collected from vein of eyeground.

The collected blood was centrifuged (2,000 rpm for five minutes), plasma was separated and the total IgE amount in the plasma was measured by means of ELISA (IgE Mouse EIA Kit; Seikagaku Corporation).

In the group to which the cyclopentenone was administered, 10 mg/kg was compulsorily administered once daily from the date of antigen sensitization until the day before the blood collection.

In the control group, distilled water was orally administered by the same manner as above and the non-sensitized group was named as a non-treated group.

The result is given in Table 4. An increase in total IgE amount in plasma by sensitization with egg white albumin was suppressed by administration of the cyclopentenone.

TABLE 4

|  | Total IgE Amount in Plasma (ng/ml) Average ± SEM |
| --- | --- |
| Non-Treated Group | 0 |
| Control Group | 742.6 ± 366.0 |
| Cyclopentenone-Given Group | 355.8 ± 127.5 |

(2) Male rats of Wistar strain of five weeks age (one group consisting of five rats) (Nippon SLC) were sensitized by an intraperitoneal injection of 100µl of 0.01% solution of egg white albumin (Sigma) in an aqueous physiological saline solution and 100µl of Alum (trade name: Imject Alum; Pierce) and, after 14 days, blood was collected from abdominal artery.

The collected blood was centrifuged (at 2000 rpm for five minutes), plasma was separated and the amount of antigen-specific IgE was measured by a 48-hour rat passive cutaneous anaphylaxis (PCA) reaction.

Thus, serum was diluted with a physiological saline solution in a successively doubling manner ranging from ¼ to ¹⁄₆₄ and each 0.1 ml thereof was subcutaneously injected to hair-clipped back of male rats of Wistar strain of seven weeks age. After 48 hours from the subcutaneous injection, 1 ml of a mixture of 0.05% egg white albumin and 0.5% Evans Blue (manufactured by Nacalai Tesque) was injected from tail vein. After 30 minutes from the injection from the tail vein, rats were subjected to decapitation and to exanguinated death, blue spots appeared on the back were observed, the spots with a diameter of 5 mm or more were judged to be positive and the highest dilution was adopted as an IgE titer.

In the cyclopentenone-administered groups, 1 mg/kg or 10 mg/kg of cyclopentenone was intraperitoneally administered once daily for three days from the antigen-sensitized day while, in the control group, distilled water was intiaperitoneally administered by the same manner.

The result is given in Table 5.

TABLE 5

|  | IgE Titer |
| --- | --- |
| Control Group | 64 |
| Cyclopentenone-administered groups |  |
| 1 mg/kg/day | 16 |
| 10 mg/kg/day | <4 |

An increase in the antigen-specific IgE amount by sensitization with egg white albumin was inhibited by administration of cyclopentenone in a dose-dependent manner.

As such, the IgE production was inhibited by the cyclopentenone. Similar inhibiting activity to IgE production was noted in (−)-cyclopentenone and (+)-cyclopentenone.

Example 8

(1) C57BL/6mice (female, five weeks age) were purchased from Nippon SLC and used for the experiment after a preliminary breeding for one week at our end. Ovine erythrocyte (manufactured by Shimizu Jikken Zairyo) which is an antigen provoking the sensitivity reaction of a delayed type was washed e three times with a physiological saline solution (manufactured by Otsuka Pharmaceutical) to make $1 \times 10^9$ cells/ml and 200 µl of it was intraperitoneally injected to mice to subject to an antigen sensitization.

After five days from the sensitization, 40µl of antigen which was prepared by the same manner was injected to right paw to induce an antigen whereby pedal edema was provoked. From the antigen-sensitized date, cyclopentenone was intraperitoneally administered to mice (one group consisting of five mice) once daily at the dose of 1 mg/kg or 10 mg/kg for three days.

After two days from the antigen induction, volume of right paw of the mice was measured by a measuring device for pedal edema (manufactured by Ugo Basile) and used as an index for the sensitivity reaction of a delayed type. The measured value was given by calculating the increasing rate from the right paw volume of the mice measured before the antigen induction.

Figure 10:
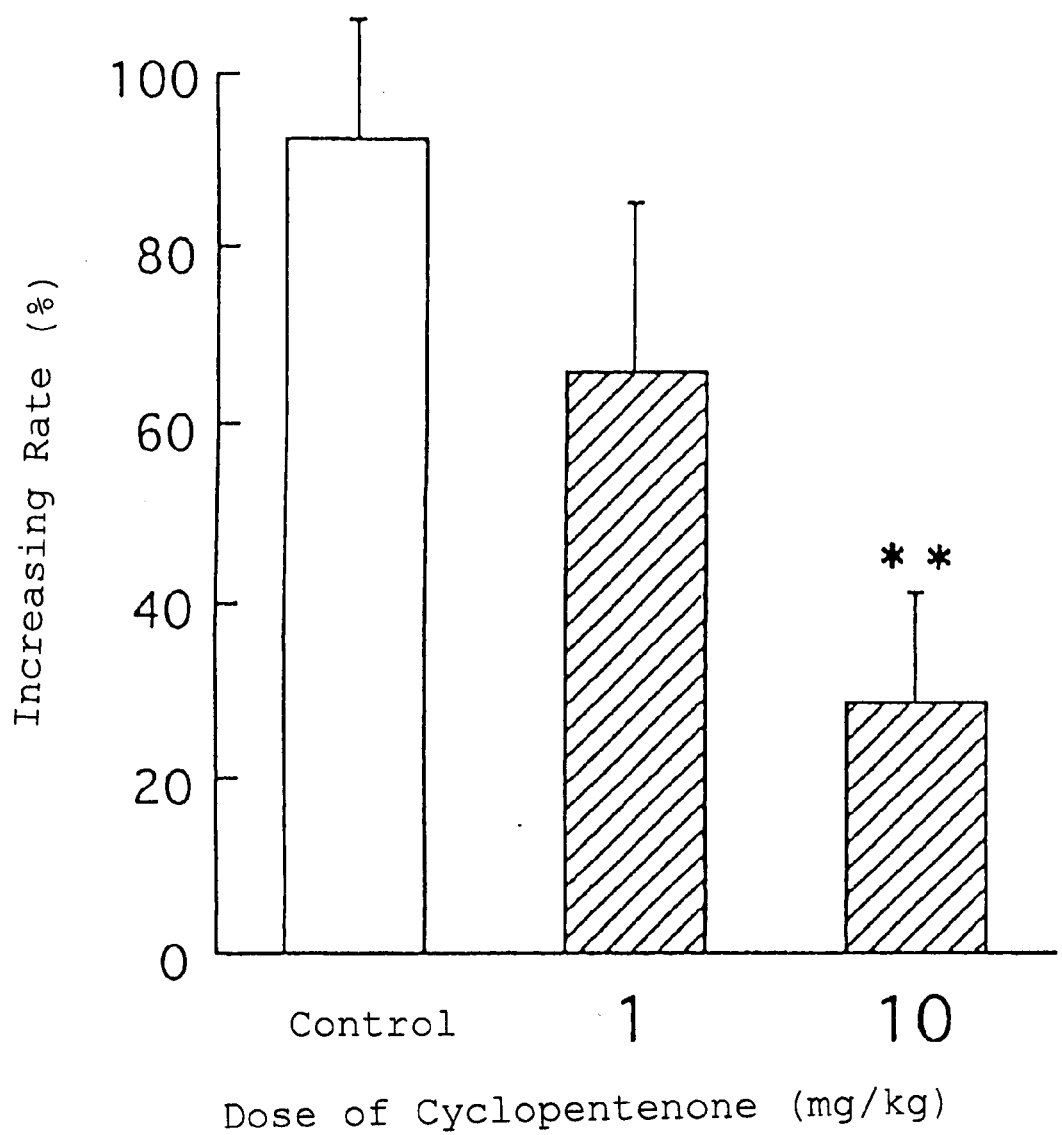
FIG. 10 shows the inhibition activity of the cyclopentenone to delayed type hypersensitivity reaction.

The result is shown in FIG. 10. Thus, FIG. 10 shows the an inhibition activity of the cyclopentenone to delayed type hypersensitivity reaction where the ordinate indicates an increasing rate (%) while the abscissa indicates a dose of the cyclopentenone (mg/kg). Incidentally, ** in the drawing means that it is significant to the control in $p<0.01$.

Administration of 1 mg/kg of the cyclopentenone suppressed the delayed type hypersensitivity reaction and administration of 10 mg/kg showed a significant inhibition activity to delayed type hypersensitivity reaction.

Incidentally, (−)-cyclopentenone and (+)-cyclopentenone showed similar effects as well.

(2) Spleen was excised from C3H/HeJ mice (Nippon SLC; male; five weeks age), finely disintegrated and suspended in an RPMI-1640 medium (manufactured by Gibco) containing 10% of fetal bovine serum (manufactured by High Clone) to give a unicellular, solution. The floating solution of the cells was planted to a plastic Petri dish, incubated at 37° C. in a carbon dioxide gas incubator for two hours, adhesive cells were removed by adhering to the Petri dish and the non-adhesive cells were used as spleen lymphocytes. The cell concentration was adjusted to $2 \times 10^6$ cells/ml and planted to a 96-well microtiter plate at 200 µl well, the cyclopentenone of various concentrations was added to each of the wells except that for the control group, then 5 µg of concanavalin A (ConA; manufactured by Nacalai Tesque) to all wells and incubation was conducted at 37° C. in a carbon dioxide gas incubator for one day. After the incubation, 1 µCi of $^3$H-thymidin was added to all cells and incubation was conducted for one day more and its amount incorporated into the cells was measured by a liquid scintillation counter.

Figure 11:
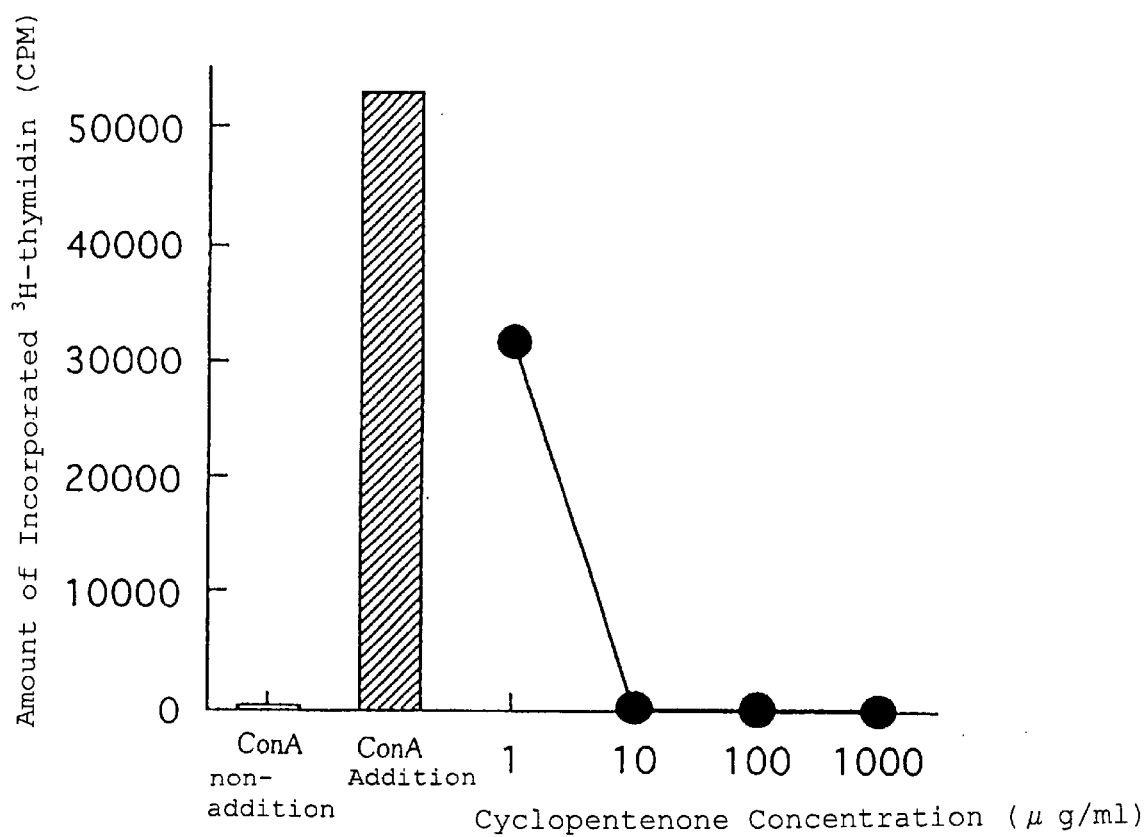
FIG. 11 shows the inhibition activity of the cyclopentenone to lymphocyte proliferation.

The result is shown in FIG. 11. Thus, FIG. 11 shows an inhibition activity of the cyclopentenone to lymphocyte proliferation where the ordinate shows the amount of incorporated $^3$H-thymidin (CPM) while the abscissa shows ConA addition, non-addition control and the cyclopentenone concentration (µg/ml). It is apparent from the drawing that the cyclopentenone shows a dose-dependent inhibition activity to lymphocyte proliferation of mice stimulated by mitogen and proliferation of lymphocytes is suppressed almost completely by 10 µg/ml whereby an inhibition activity to activation of lymphocytes was noted.

Incidentally, (−)-cyclopentenone and (+)-cyclopentenone showed the similar effects as well.

(3) Spleen was excited from BALB/c mice (Nippon SLC; male; five weeks age) an C57BL/6 mice (Nippon SLC; male; five weeks age) and spleen lymphocytes were prepared by the above-mentioned method. Concentration of each of the cell floating solutions was adjusted to $2\times10^6$ cells/ml and each 100 µl was mixed and planted to a 96-well microtiter plate. The cyclopentenone of various concentrations was added to each of the wells except that for the control group and incubated at 37° C. in a carbon dioxide gas incubator for four days. After the incubation, 1 µCi of $^3$H-thymidin was added to each of the wells and incubated for one day more and the incorporated amount into the cells was measured by a liquid scintillation counter.

Figure 12:
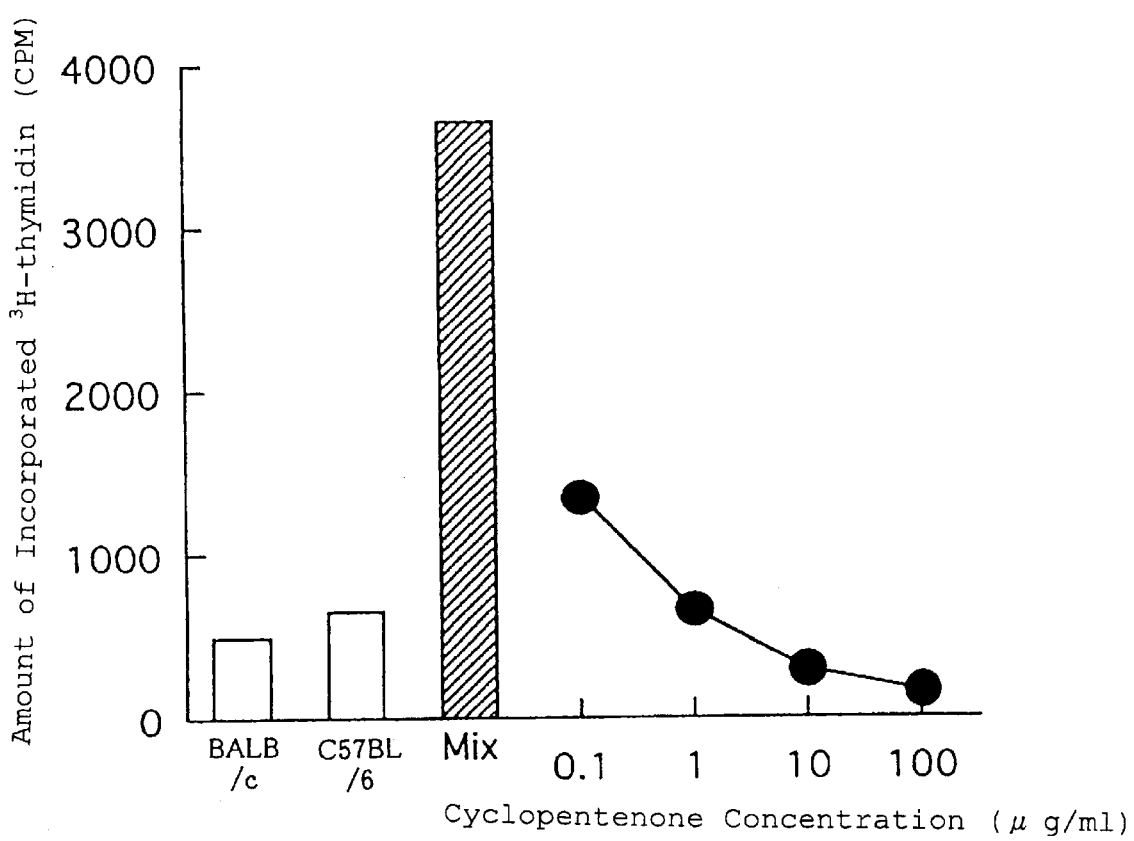
FIG. 12 shows the inhibition activity of the cyclopentenone to mixed lymphocyte reaction.

The result is shown in FIG. 12. Thus, FIG. 12 shows the inhibition activity of the cyclopentenone to a mixed lymphocyte reaction where the ordinate shows the amount of incorporated $^3$H-thymidin (CPM) while the abscissa shows the control of BALB/c spleen lymphocytes (shown as BALB/c in the drawing), the control of C57BL/6 spleen lymphocytes (shown as C57BL/6 in the drawing), the mixed control of BALB/c spleen lymphocytes and C57BL/6 spleen lymphocytes and the cyclopentenone concentrations (µg /ml). It is apparent from the drawing that the cyclopentenone shows a dose-dependent inhibition activity to lymphocytes activated by allogeneic antigen stimulation and almost complete suppression is noted by 10 µg/ml whereby an inhibition activity to activation of lymphocyte by a mixed lymphocyte reaction was noted.

Incidentally, (−)-cyclopentenone and (+)-cyclopentenone showed the similar inhibition activity to mixed lymphocyte reaction.

Example 9

(1) One µl of 0.25 µg/µl pBR322 DNA (manufactured by Takara Shuzo) was added to a mixture of 2µl of topoisomerase II (manufactured by TopoGEN, 2 units/µl), 2 µl of a buffer with a ten-fold diluted concentration [0.5M Tris-HCl (pH 8.0), 1.2M KCl, 0.1M $MgCl_2$, 5 mM adenosine triphosphate and 5 mM dithiothreitol], 2 µl of 0.1% bovine serum albumin (manufactured by Takara Shuzo), 11 µl of distilled water and 2 µl of distilled water (a control) or a sample (50, 100, 200, 500, 1000 or 2500 µM of cyclopentenone) and made to react at 37° C. After the reaction for 30 minutes, the reaction was stopped by adding 2 µl aqueous solution of 1% sodium dodecylsulfate, 50% glycerol and 0.02% Bromophenol Blue.

The above reaction solution (20 µl) was applied to 1% agarose gel prepared from agarose L03 (manufactured by Takara Shuzo) and TAE buffer [40 mM Tris, 5 mM sodium acetate and 1 mM disodium ethylenediaminetetraacetate (EDTA); adjusted to pH 7.8 with acetic acid] and electrophoresis was conducted in the TAE buffer. After the electrophoresis, the gel was dipped in an aqueous solution of 1 µg/ml ethidium bromide and irradiated with ultraviolet ray to observe the electrophoretic pattern of DNA. In a control which was an aqueous solution, DNA completely change from a supercoiled type to a relaxation type but, when topoisomerase II activity was inhibited, the change from a supercoiled type to a relaxation type was partially or completely inhibited.

The result is shown in Table 6.

TABLE 6

| Concentration (µM) in Reaction Solution | Inhibition Activity |
| --- | --- |
| 0 | — |
| 10 | — |
| 20 | ++ |
| 50 | ++ |
| 100 | +++ |
| 250 | +++ |

In the control where water was added, DNA completely change from a supercoiled type to a relaxation type but, when the concentration cyclopentenone was 20 µM or higher, the change of DNA from a supercoiled type to a relaxation type was partially or completely inhibited whereby the activity of cyclopentenone for inhibiting the topoisomerase II was ascertained. In Table 6, − means a complete change from a supercoiled type to a relaxation type; + means a change in a medium degree; ++ means that most of supercoiled type remained; and +++ means that there was no decrease in a supercoiled type at all.

(2) Activity of cyclopentenone for inhibiting the topoisomerase I was measured by the same method as in Example 9-(1) except that topoisomerase I [manufactured by TopoGEN, 0.01 unit/µg 1] was used instead of topoisomerase II; and 100 mM Tris-HCl (pH 7.9), 10 mM EDTA, 1 mM spermidine and 50% glycerol were used as a buffer with a ten-fold diluted concentration. Incidentally, as a sample, the cyclopentenone was added to make the final concentration 1 mM.

The result was that topoisomerase I was inhibited by 1 mM cyclopentenone.

As such, the cyclopentenone showed an inhibiting activity to topoisomerase II which was expressed only transiently during amitotic phase in normal cells but became to be expressed highly through whole cell cycle by canceration, and also to topoisomerase I which increases in its expressing amount and activity by canceration. (−)-Cyclopentenone and (+)-cyclopentenone gave the similar results as well.

Example 10

Injection Preparations (1) Cyclopentenone was added to a physiological saline solution (as listed in the Japanese Pharmacopoeia) in a concentration of 1% to prepare an injection preparation.

(2) (−)-Cyclopentenone and glycyrrhizic acid were added to a physiological saline solution (the same as above) in concentrations of 0.5% and 0.1%, respectively, to prepare an injection preparation.

Example 11

Tablets (1) A tablet containing 100 mg of cyclopentenone and an appropriate amount of microcrystalline cellulose was prepared and coated with sugar to manufacture a tablet preparation.

(2) A tablet containing 0.1 mg of (+)-cyclopentenone, 10 mg of dipotassium glycyrrhizinate and an appropriate amount of microcrystalline cellulose was prepared and coated with sugar to manufacture a tablet preparation.

Example 12

(1) Pectin (Pomosin Pectin LM-13CG; manufactured by Hercules) (5 kg) was added to 100 liters of tap water and the mixture was heated from the liquid temperature of 28° C. to 120° C. by means of blowing steam thereinto during 35 minutes, kept at 120° C. for five hours with stirring and cooled to prepare 135 liters of cooled mixture. To this were added 1.35 kg of Celite #545 (manufactured by Celite) and 1.35 kg of Silica #600-S (manufactured by Chuo Silica) as filter aids and filtration was conducted using a compact filter (6-inch filter paper in 16 stages; ADVANTEC #327) precoated with 0.1 kg of Celite #545 and 0.1 kg of Silica #600-S. The resulting filtrate was subjected to a continuous instant heating treatment (at 98° C. for 60 seconds) using a plate heater (manufactured by Nichihan Seisakusho) followed by cooling to prepare 150 liters of heat-treated pectin solution containing the cyclopentenone.

Said heat-treated pectin solution containing the cyclopentenone had pH of about 3.5, acidity of 6.2 ml and sugar degree of 5.8 Brix %. Incidentally, pH was measured by a pH meter, acidity was expressed in terms of the amount (ml) of 0.1N NaOH used for neutralizing to pH 7.0 and sugar degree was measured by a Brix saccharometer.

(2) Beverage was prepared according to the following formulation.

| Fructose-Glucose-Liquid Sugar | 5.00% |
|---|---|
| Sugar | 4.00% |
| Acidic agent | 1.20% |
| Perfumes | 0.30% |
| Cyclopentenone-containing material | 0.5% |
| Pure water | balance |
| Total | 100.00% |

The heat-treated pectin solution containing the cyclopentenone mentioned in Example 12-(1) was used as the cyclopentenone-containing material and its amount calculated on a solid basis was added. This beverage (100 ml) contains 4 mg of the cyclopentenone.

Merit of the Invention

In accordance with the present invention, a pharmaceutical containing at least one compound selected from the cyclopentenone or optically active substances thereof or salts thereof as an effective component is offered. Said pharmaceutical is quite useful as an antirheumatic agent or a preventive agent for rheumatism and as a therapeutic agent or a preventive agent for diseases accompanied by inflammation as an anti-inflammatory agent or a preventive agent for inflammation by control of inflammatory cytokine. In addition, it is now possible in accordance with the present invention that an appropriate amount of the cyclopentenone or optically active substance thereof or salt thereof having a physiological activity is contained in food or in beverage. Because of the physiological function of those compounds, the functional food or beverage of the present invention has an improving action and/or a preventive action to symptoms of rheumatism, particularly chronic articular rheumatism, whereby it is quite useful for therapy, prevention, etc. of complications by rheumatism, difficulty in walking, etc. In addition, due to an inhibition activity to inflammatory cytokine, the food or beverage of the present invention is useful for improvement or prevention of symptoms of the diseases accompanied by inflammation.

Further, production of tumor necrosis factor is suppressed by the pharmaceutical of the present invention and the pharmaceutical of the present invention is useful for therapy or prevention of diseases such as the diseases mediated by production of tumor necrosis factor, diseases worsened by production of said factor, sepsis, AIDS, chronic articular rheumatism, etc. Furthermore, the food or beverage of the present invention is quite useful for improving the symptoms of the diseases such as the diseases mediated by production of tumor necrosis factor, diseases worsened by production of said factor, sepsis, AIDS, chronic articular rheumatism, etc. and also for preventing said diseases. Thus, the method of the present invention using at least one compound selected from the cyclopentenone, optically active substances thereof and salts thereof as an effective component is quite useful for controlling the producing amount of tumor necrosis factor.

Moreover, the present invention offers a pharmaceutical containing the cyclopentenone, optically active substance thereof or salt thereof having an inhibition activity to NO production and said pharmaceutical is useful for the therapy or prevention of the diseases which require the suppression of production of NO such as systemic blood pressure reduction, blood pressure response reduction, autoimmune diseases, inflammation, arthritis, rheumatic arthritis, inflammatory intestinal diseases, blood vessel function insufficiency, etiologic blood vessel dilation, tissue injury, cardiovascular ischemia, hypersensitivity to pain, cerebral ischemia, diseases accompanied by neovascularization and cancer and also for keeping the homeostasis of living organisms.

In addition, an inhibitor for NO production, an inhibitor for neovascularization, a preventive agent for carcinogenesis, anticancer agent, anti-inflammatory agent and an improving agent for ischemic brain injury containing at least one compound selected from the cyclopentenone, optically active substance thereof and salt thereof are offered as well. Said inhibitor for NO production is also useful in biochemical research and in screening of the drugs.

In accordance with the present invention, it is now possible that an appropriate amount of the cyclopentenone, optically active salt thereof or salt thereof having a physiological activity is contained in food and in beverage. Because of the inhibition activity of the cyclopentenone or optically active substance or salt thereof to the production of NO, the food or beverage of the present invention is a healthy food or beverage having a function of keeping the homeostasis of living body mediated by the NO production inhibition activity such as prevention of carcinogenesis, anticancer action, anti-inflammatory action, improving action to ischemic brain injury and potentiation of biophylaxis action.

The present invention offers an inducing agent for Fas antigen production containing at least one compound selected from the cyclopentenone or optically active substance thereof or salt thereof as an effective component; a method of inducing the Fas antigen production useful in the study of physiological function of Fas antigen or in the investigation of antagonists using those compounds as effective components; and a preventive or a therapeutic agent for the diseases accompanied by abnormal Fas antigen production such as autoimmune diseases and articular rheumatism.

Further, the food or beverage containing an effective amount of at least one compound selected from the cyclopentenone or optically active substance thereof and salt thereof is a functional food or beverage of the present invention because of the action of those compounds for inducing the Fas antigen production and is quite useful for improving the symptoms and for preventing the onset of the above-mentioned diseases. Furthermore, the cyclopentenone or optically active substance thereof or salt thereof has an apoptosis-inducing activity to synovial cells and the pharmaceutical, food or beverage of the present invention is particularly useful as an antirheumatic pharmaceutical, food or beverage.

The present invention offers an immunomodulating agent containing at least one compound selected from the cyclopentenone, optically active substance thereof and salt thereof having an inhibition activity to IgE production, an inhibition activity to delayed type hypersensitivity reaction, an inhibition activity to lymphocyte proliferation and an inhibition activity to a mixed lymphocyte reaction.

Because of the immunomodulating action of the cyclopentenone, optically active substance thereof or salt thereof, food or beverage containing a compound selected from those compounds is useful for improvement of symptoms of the diseases which require modulation of immune function such as autoimmune disease or for prevention of immune abnormality as an immunomodulating food or an immunomodulating beverage.

In addition, the method of the present invention is useful for modulation of productive amount of IgE and also for immunomodulation.

The present invention further offers an inhibitor for topoisomerase containing at least one compound selected from the cyclopentenone, optically active substance thereof and salt thereof as an effective component and also a method for inhibiting the topoisomerase containing at least one compound selected those compounds as an effective component. Said topoisomerase inhibitor is useful as an anticancer drug and said topoisomerase inhibiting method is useful in biochemical study, screening of anticancer drugs, etc.

What is claimed is:

1. A method for treatment or prophylaxis of inflammatory diseases, the method comprising administering to an individual in need of the treatment or the prophylaxis at least one compound selected from the group consisting of 4,5-dihydroxy-2-cyclopenten-1-one of formula (I)

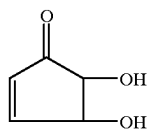

(I)

an optically active compound thereof and a salt thereof as an effective component.

2. The method as claimed in claim 1, wherein the disease is selected from the group. consisting of rheumatism, inflammation, disease mediated or worsened by tumor necrosis factor, disease requiring the suppression of production of nitrogen monooxide, disease accompanied by neovascularization, cancer, ischemic brain injury, disease accompanied by abnormal Fas antigen production, and disease requiring topoisomerase inhibition.

3. The method according to claim 1, wherein said effective component is administered as a pharmaceutical agent.

4. The method according to claim 1, wherein said effective component is administered as a food or a beverage.

* * * * *

UNITED STATES PATENT AND TRADEMARK OFFICE
CERTIFICATE OF CORRECTION

PATENT NO. : 6,284,801 B1
DATED : September 4, 2001
INVENTOR(S) : Nobuto Koyama et al.

It is certified that error appears in the above-identified patent and that said Letters Patent is hereby corrected as shown below:

Please change the filing date of the international application from March 10, 1998 to:

-- PCT Filed: Mar. 18, 1998 --

Signed and Sealed this

Second Day of April, 2002

Attest:

JAMES E. ROGAN
Director of the United States Patent and Trademark Office

Attesting Officer